(12) United States Patent
Moshaverinia et al.

(10) Patent No.: US 10,667,994 B2
(45) Date of Patent: Jun. 2, 2020

(54) BIOACTIVE DENTAL RESTORATIVE MATERIAL WITH REMINERALIZATION PROPERTIES

(71) Applicant: The Regents of the University of California, Oakland, CA (US)

(72) Inventors: Alireza Moshaverinia, Los Angeles, CA (US); Mohammad Mahdi Hasani-Sadrabadi, Los Angeles, CA (US); Tara L. Aghaloo, Sherman Oaks, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/256,566

(22) Filed: Jan. 24, 2019

(65) Prior Publication Data
US 2019/0274932 A1    Sep. 12, 2019

Related U.S. Application Data

(60) Provisional application No. 62/641,137, filed on Mar. 9, 2018.

(51) Int. Cl.
*A61K 6/08*    (2006.01)
*A61K 6/889*   (2020.01)
*A61K 6/17*    (2020.01)

(52) U.S. Cl.
CPC ............... *A61K 6/889* (2020.01); *A61K 6/17* (2020.01)

(58) Field of Classification Search
CPC .................................................. A61K 6/0835
See application file for complete search history.

(56) References Cited

U.S. PATENT DOCUMENTS

| 7,091,259 B2 | 8/2006 | Bui et al. |
| 2002/0129736 A1 | 9/2002 | Bui et al. |
| (Continued) | | |

OTHER PUBLICATIONS

Wilson et al., "The glass-ionomer cement, a new translucent dental filling material", Journal of Applied Chemistry and Biotechnoiogy, 1971, Nov. 1971, 21(11):313.
(Continued)

*Primary Examiner* — Michael F Pepitone
(74) *Attorney, Agent, or Firm* — Mark S. Cohen; Pearl Cohen Zedek Latzer Baratz LLP

(57) ABSTRACT

Conventional dental cements lack certain properties such as the facilitation of optimal re-mineralization. The novel bioactive glass-ionomer dental and bone cement formulations disclosed herein induces mineralization at the in vivo interface and exhibits superior handling properties (shorter setting time) and mechanical properties (improved bond strength to dentin and flexural strength). The present invention presents the first bioactive glass-ionomer dental cement with mineralization power, exhibiting improved bond strength to tooth structure, sharp setting time and superior mechanical strength. Materials of this invention can be used as bone cement, as a dental filling (restorative material), as a liner for deep cavity preparations (to avoid root canal therapies and tooth sensitivity), or as a luting cement to cement dental crowns. Moreover, it can be utilized in a flowable resin for use as a coating to prevent dental caries in their initial steps (white spots).

22 Claims, 17 Drawing Sheets

(56) References Cited

U.S. PATENT DOCUMENTS

| | | | |
|---|---|---|---|
| 2006/0084717 A1* | 4/2006 | Cohen | A61K 6/0023 523/116 |
| 2012/0171640 A1* | 7/2012 | Guy | A61C 13/0022 433/203.1 |
| 2014/0088308 A1* | 3/2014 | Xu | C07C 237/22 546/6 |
| 2016/0030323 A1 | 2/2016 | Brody et al. | |
| 2016/0046815 A1* | 2/2016 | Messersmith | C09D 5/1681 210/688 |
| 2016/0331564 A1 | 11/2016 | Kangas | |
| 2017/0326272 A1 | 11/2017 | Harding et al. | |

OTHER PUBLICATIONS

Moshaverinia et al., "A review of polyelectrolyte modifications in conventional glass-ionomer dental cements", Journal of Materials Chemistry, 2012;22(7):2824-33.

Crisp et al., "Properties of improved glass-ionomer cement formulations", Journal of Dentistry, May 1, 1975;3(3):125-30.

Moshaverinia et al., "A review of powder modifications in conventional glass-ionomer dental cements", Journal of Materials Chemistry, 2011;21(5):1319-28.

Causton, "The physico-mechanical consequences of exposing glass ionomer cements to water during setting", Biomaterials, Apr. 1, 1981;2(2):112-5.

Davidson, "Advances in glass-ionomer cements", Journal of Applied Oral Science, 2006;14(SPE):3-9.

Smith, "Development of glass-ionomer cement systems", Biomaterals. Apr. 1, 1998;19(6):467-78.

McLean et al., "Proposed nomenclature for glass-ionomer dental cements and related materials", Quintessence Int. 1994;25(9):587-9.

Sidhu et al., "A review of glass-ionomer cements for clinical dentistry", Journal of Functional Biomaterials, 2016;7(3):16, 15 pages.

Nicholson, "Adhesion of glass-ionomer cements to teeth: a review", International Journal of Adhesion and Adhesives, Sep. 1, 2016;69:33-8.

Lohbauer, "Dental glass ionomer cements as permanent filling materials?—Properties, limitations and future trends", Materials, Dec. 28, 2009;3(1):76-96.

Walls, "Glass polyalkenoate (glass-ionomer) cements: a review", Journal of Dentistry, Dec. 1, 1986;14(6):231-46.

Ching et al., "Modification of glass ionomer cements on their physical-mechanical and antimicrobial properties", Journal of Esthetic and Restorative Dentistry, Nov. 5, 2018: 1-15.

Moshaverinia et al., "Effects of incorporation of hydroxyapatite and fluoroapatite nanobioceramics into conventional glass ionomer cements (GIC)", Acta Biomaterialia, Mar. 1, 2008;4(2):432-40.

Moshaverinia et al., "Synthesis and characterization of a novel N-vinylcaprolactam-containing acrylic acid terpolymer for applications in glass-ionomer dental cements", Acta Biomaterialia, Jul. 1, 2009;5(6):2101-8.

Moshaverinia et al., "Synthesis and characterization of a novel fast-set proline-derivative-containing glass ionomer cement with enhanced mechanical properties", Acta Biomaterialia, Jan. 1, 2009;5(1):498-507.

Lee et al., "Mussel-inspired surface chemistry for multifunctional coatings", Science, Oct. 19, 2007; 318(5849):426-30.

Lucas et al., "Toughness, bonding and fluoride-release properties of hydroxyapatite-added glass ionomer cement", Biomaterials, Sep. 1, 2003; 24(21):3787-94.

Yi et al., "Flexible fiber-reinforced composites with improved interfacial adhesion by mussel-inspired polydopamine and poly(methyl methacrylate) coating", Materials Science and Engineering C, 2016, vol. 58, pp. 742-749.

International Search Report and Written Opinion, dated Jul. 5, 2019, from corresponding International Application No. PCT/US19/21473.

* cited by examiner

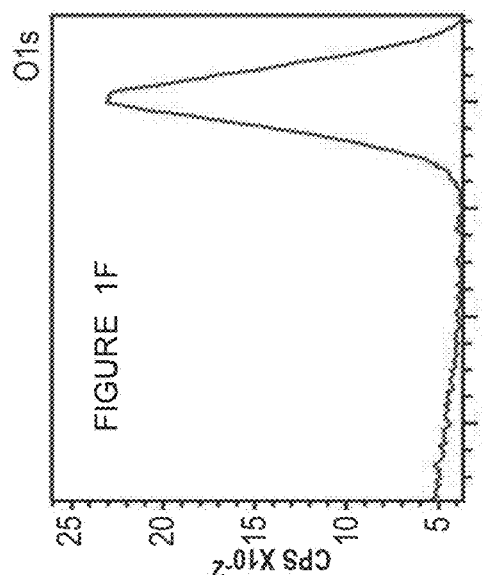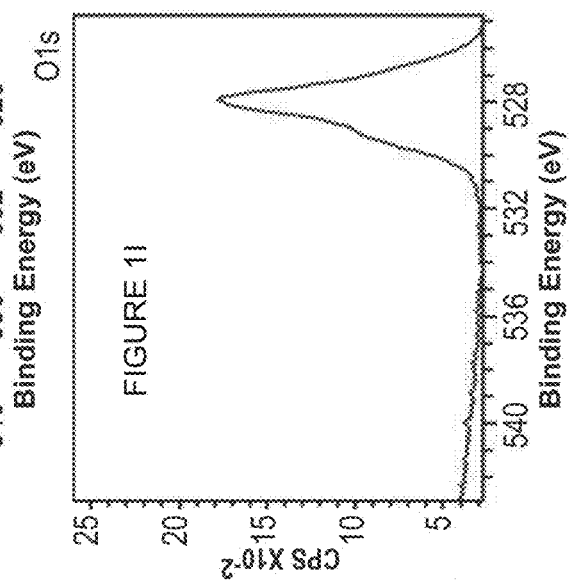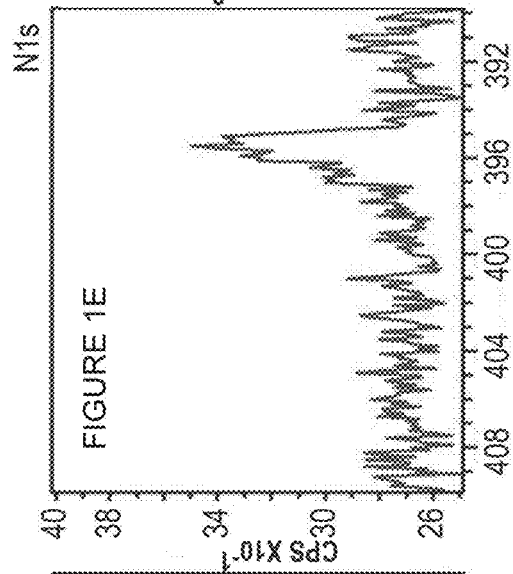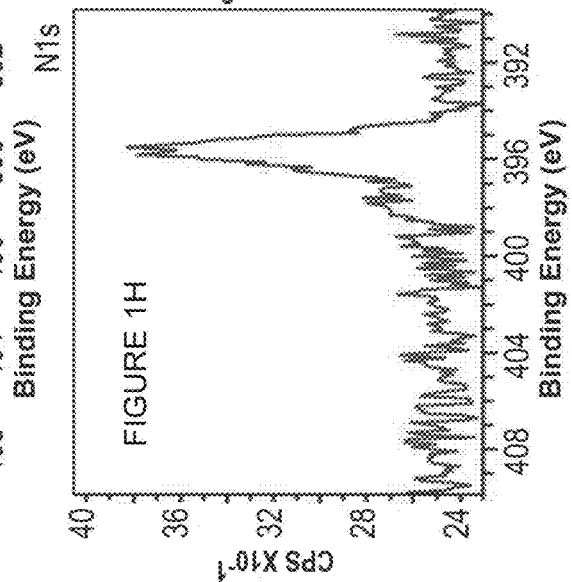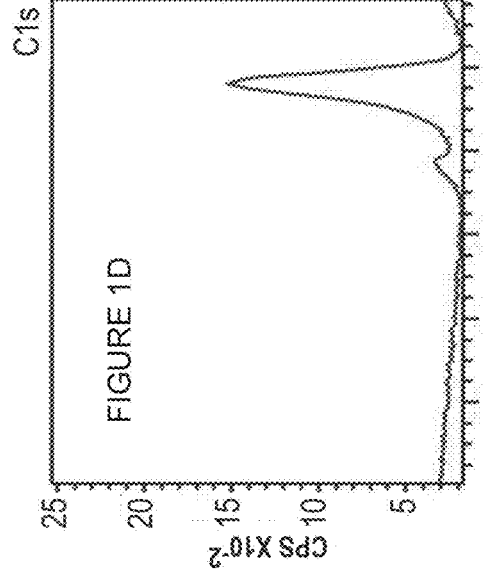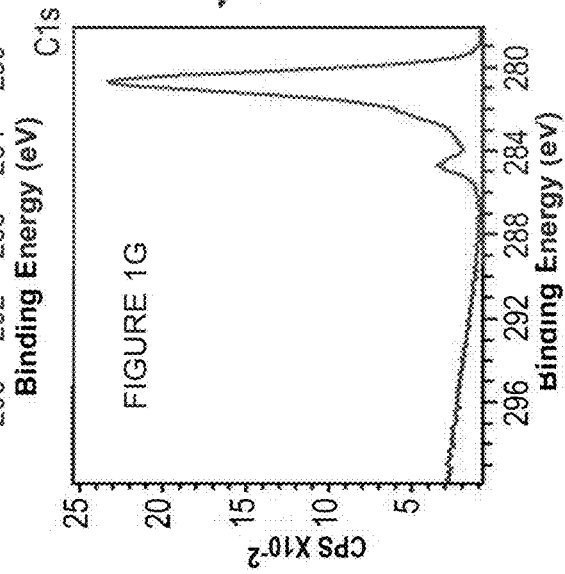

Without conditioner

HAp formation at the interface

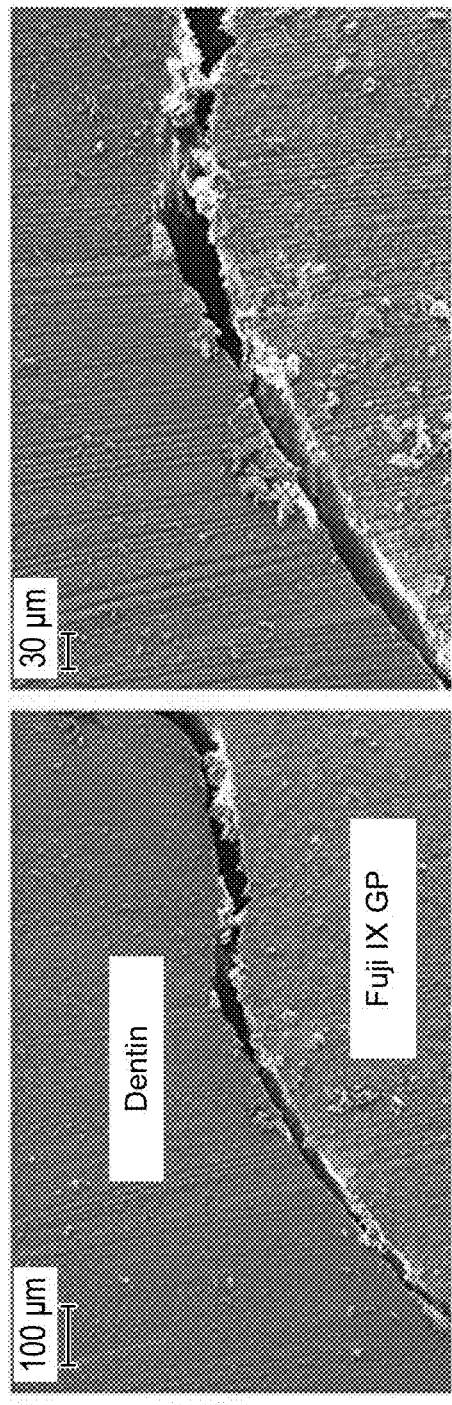
FIGURE 4I
FIGURE 4J
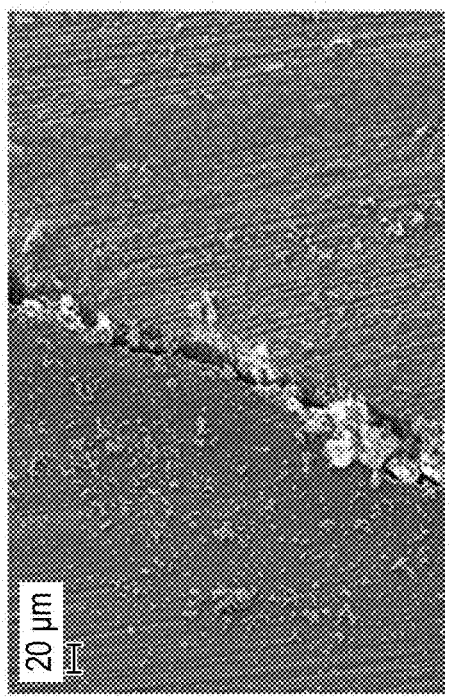
FIGURE 4K

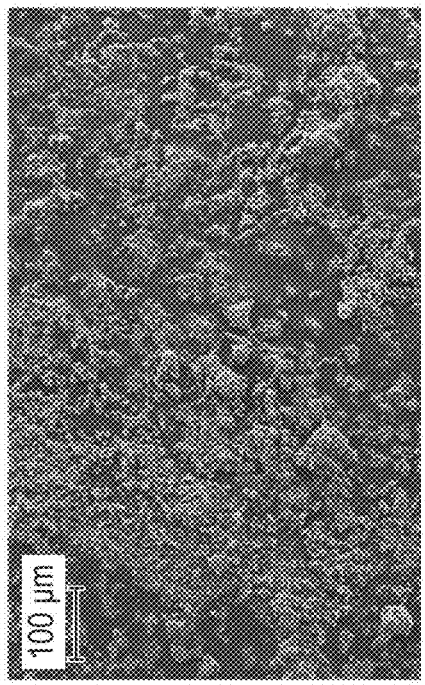
FIGURE 5A
No PDA + Resin
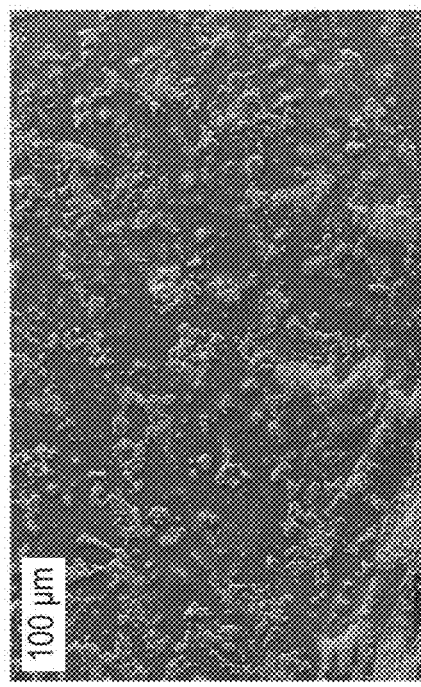
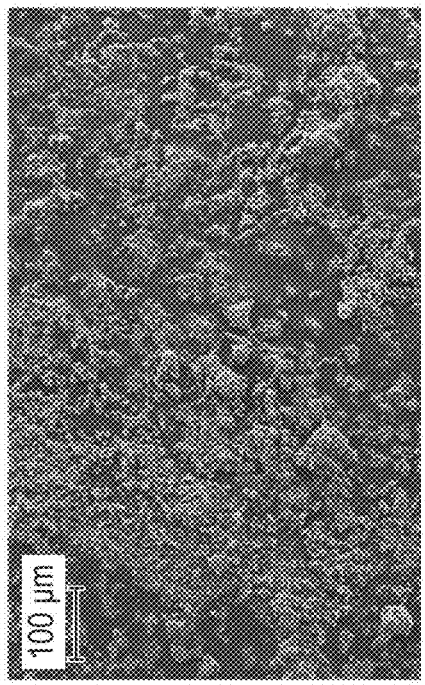
FIGURE 5B
PDA + Resin
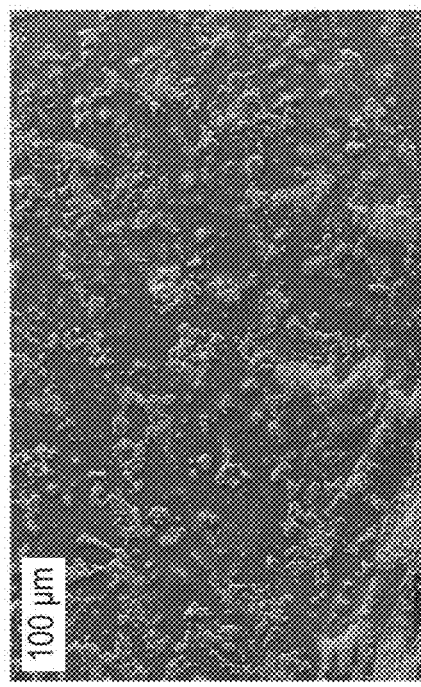
FIGURE 5A
No PDA + Resin
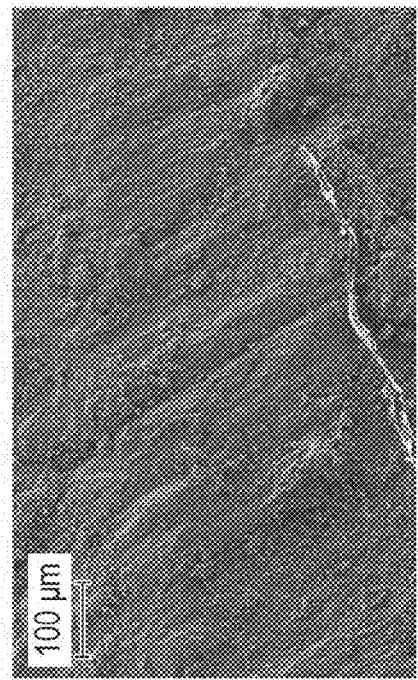
FIGURE 5C
No resin + No PDA

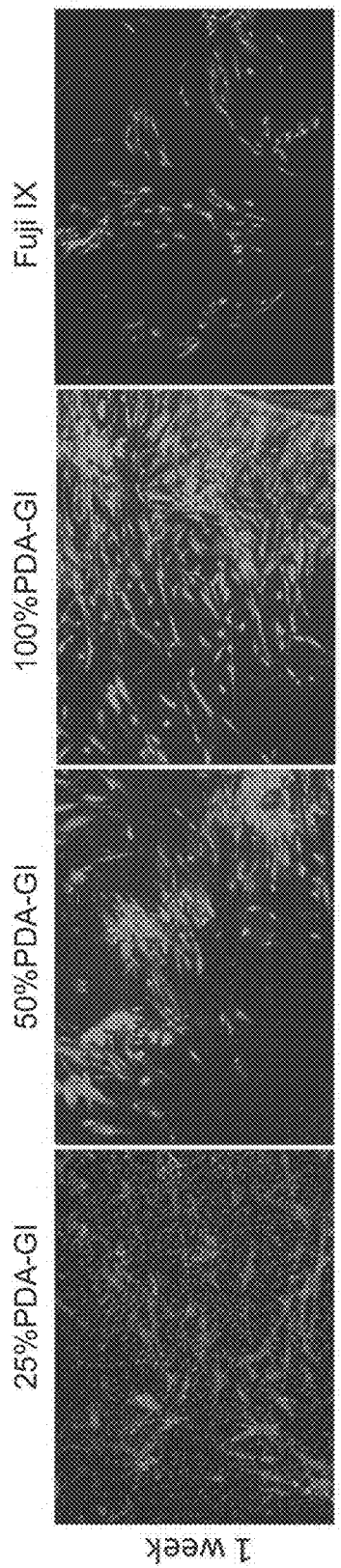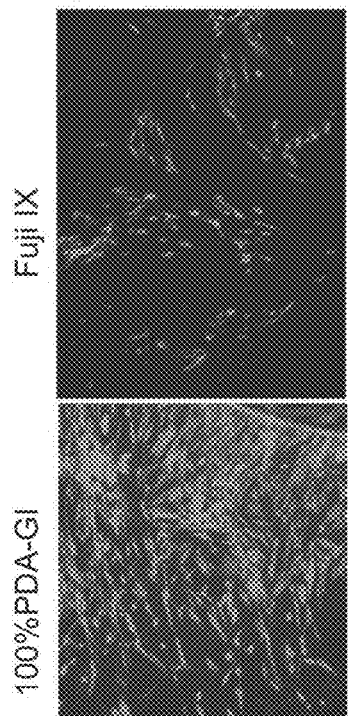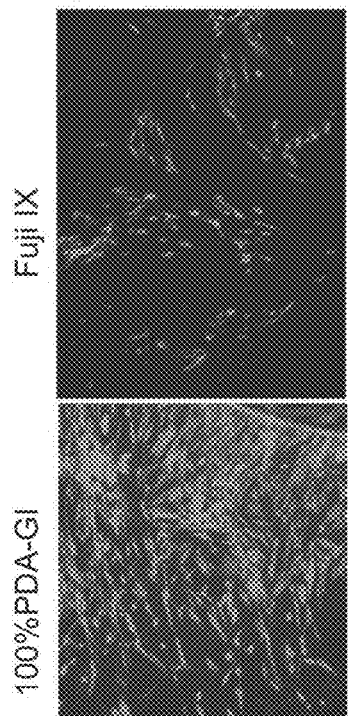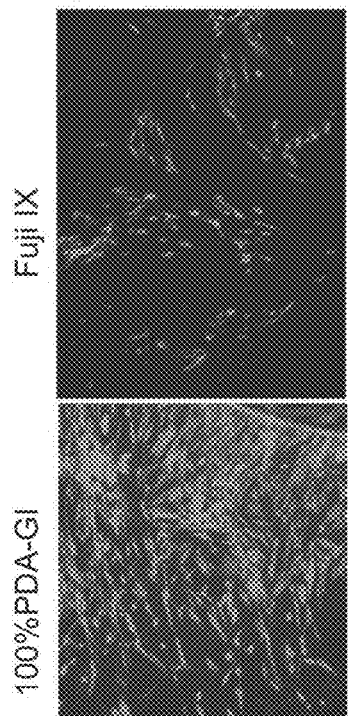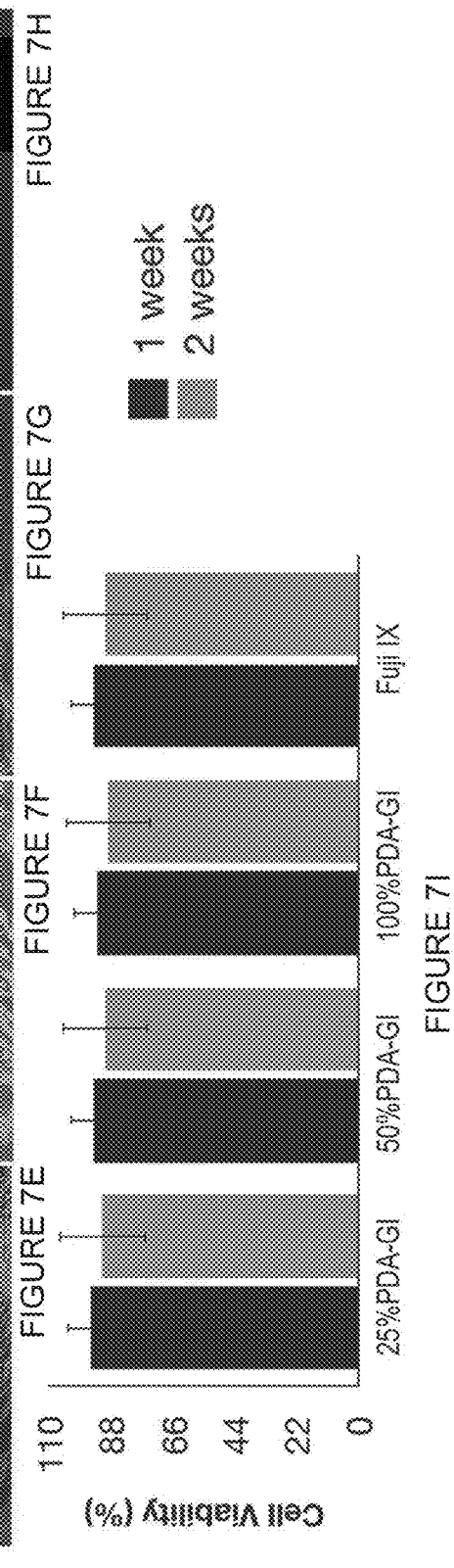

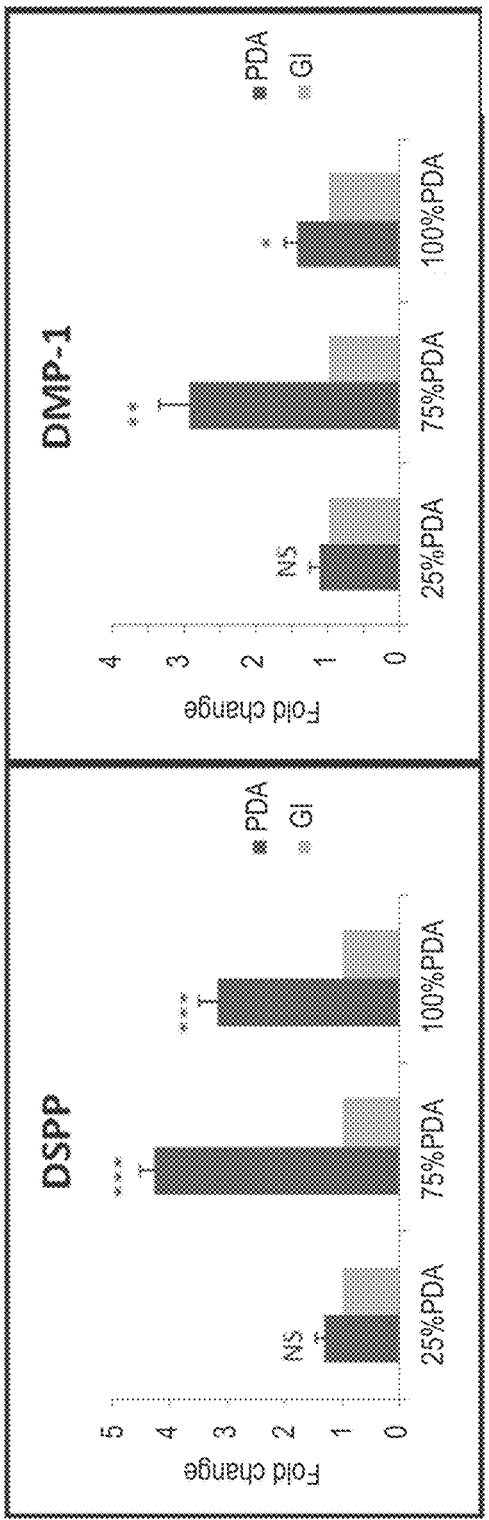
FIGURE 8A
FIGURE 8B
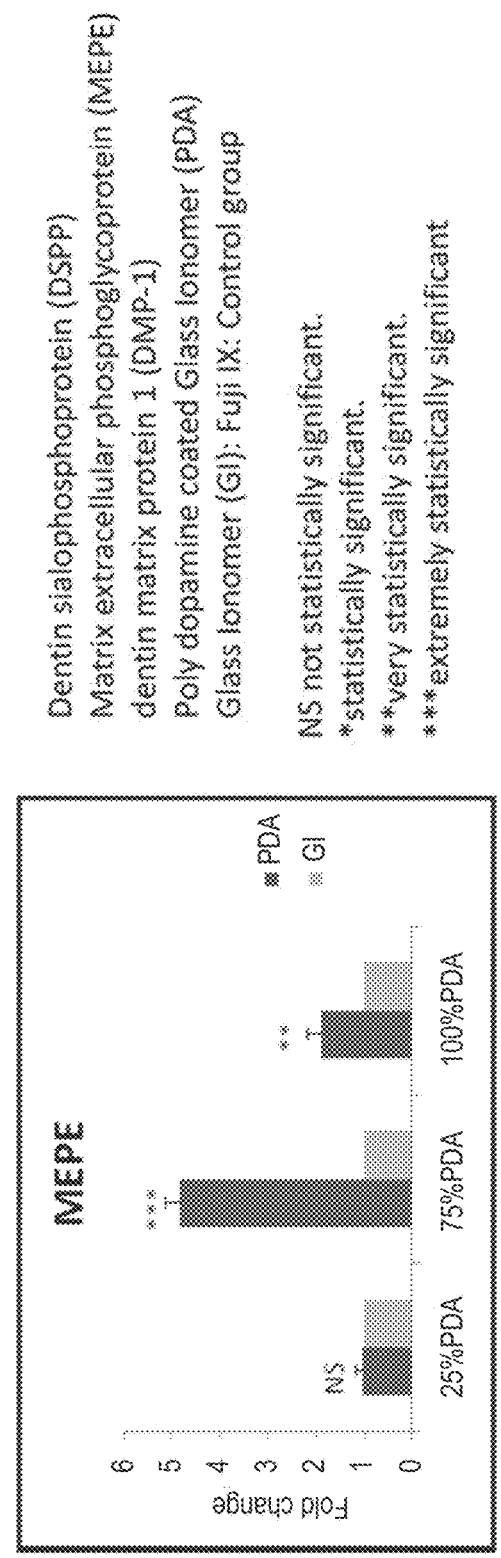
FIGURE 8C

BIOACTIVE DENTAL RESTORATIVE MATERIAL WITH REMINERALIZATION PROPERTIES

CROSS REFERENCE TO RELATED APPLICATIONS

This application claims the benefit of U.S. Ser. No. 62/641,137, filed on Mar. 9, 2018 (and entitled Bioactive Dental Restorative Material with Remineralization Properties), which is incorporated in their entirety herein by reference.

FIELD OF THE INVENTION

The present invention relates to dental adhesive compositions and methods for making and using them.

BACKGROUND OF THE INVENTION

Glass-ionomer cements (GICs) are known to be useful as dental restorative materials. GICs are formed from glass ionomer powders which comprise finely ground ceramic powders, the main components of which are silica (SiO2), alumina (Al2O3) and calcium fluoride (CaF2) as flux, sodium fluoride (NaF) and cryolite (Na3AlF6) or aluminum phosphate (AlPO4). Phosphate and fluoride salts are used to modify and control the setting characteristics of the cement. GICs are, in general, formed predominantly from alumina and silica, which form the back-bone of the glass. Glass-ionomer cements are formed by the reaction of an ion-leachable alumino-silicate glass powder with an aqueous solution of polyacid such as polyacrylic acid (polyalkenoic acid). GICs are well-known for their properties of direct adhesion to tooth structure and base metals; for anti cario-genicity due to release of fluoride; low shrinkage resulting in minimized microleakage at the tooth-enamel interface; biological compatibility and low cytotoxicity.

However, conventional GICs suffer from a number of disadvantages such as lack of re-mineralization properties, low bond strength to tooth structure, long setting time, brittleness, poor compressive strength and poor fracture resistance, all of which limit their utility. Consequently, there is a need to improve the biological and physical properties of glass ionomer cements (GICs).

SUMMARY OF THE INVENTION

The present invention provides bioactive restorative materials and methods for making and using them. More specifically, the invention relates to the development of novel polydopamine (PDA)-modified fluoroaluminosilicate glass bio-ceramic particle compositions, and the utilization of these compositions in dental applications and orthopedic applications (e.g. as a bone cement for expedited fracture healing and bone regeneration/repair for skeletal defects). As disclosed below, the glass-ionomer cement formulations disclosed herein can stimulate mineral hydroxyapatite formation and natural re-mineralization processes at for example cement-tooth interfaces. Additionally, due to the manner in which polydopamine is used in the compositions of the invention, this cement exhibits a superior bond strength to dentin tooth structures, as well as a number of other highly desirable mechanical properties.

As described below, the cement compositions disclosed herein can induce tertiary dentin formation, reduce sensitivity, prevent secondary caries, as well as prevent microleakage. Embodiments of this novel glass-ionomer dental cement are formed to have a well-defined setting time, and can be used as a restorative material, cavity liner, or a luting cement. Additionally, because the glass-ionomer formulation can regenerate a layer of hydroxyapatite on the surface of teeth and bond to tooth structure, this material can be used in a variety of dental procedures such as those involving direct/indirect pulp capping.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 1D-1F show XPS analysis for various atoms of a sample comprising Fuji IX GP; FIGS. 1G-1I show XPS analysis for various atoms of a sample comprising PDA-GIC; the XPS analysis in FIG. 1B-FIG. 1I confirms the formation of a layer of PDA on the surface of aluminofluorosilicate glass particles.

FIG. 2A: Compressive strength, FIG. 2B: Flexural strength, FIG. 2C: Shear bond strength and FIG. 2D: Surface hardness. FIG. 2E: Analysis of the setting time and working time confirms the formation of a fast set cement while giving enough working time to the clinician. FIGS. 2F and 2G: Confirmation of significant improvement in the bond strength of the invented restorative material by a cohesive failure mode in cement in comparison to an adhesive mode of failure for the control group, *p<0.05. NS: Not significant; FIG. 2F: PDA-GIC; FIG. 2G: Fuji IX GP.

FIG. 3A PDA-GIC 1 day scale bar=100 µm; FIG. 3B PDA-GIC 1 day scale bar=20 µm.

3H PDA-GIC 1 day scale bar=2 µm.

FIG. 5A, no PDA+resin, FIG. 5B, PDA+Resin, FIG. 5C, No PDA+no resin; the PDA microparticles were incorporated into a HEMA (hydroxyethyl methacrylate) resin and applied on the surface of enamel. After the resin was set using a blue light curing unit, the samples were placed in artificial saliva and after 1 day the enamel surfaces were analyzed using SEM. The results clearly showed the presence of extensive amounts of the mineralization on the surface of enamel specimens that were treated with PDA-containing coating. SEM images EHT=10.00 kV.

FIGS. 7A-7I: Biocompatibility of PDA-GIC: Qualitative and quantitative analysis of viability of DPSCs using Live/Dead assay. No statistically difference was found at tested time intervals, FIG. 7A 25% PDA-GI one week, FIG. 7B 50% PDA-GI one week, FIG. 7C 100% PDA-GI one week, FIG. 7D Fuji IX one week; FIG. 7E 25% PDA-GI two weeks, FIG. 7F 50% PDA-GI two weeks, FIG. 7G 100% PDA-GI two weeks, FIG. 7H Fuji IX two weeks; FIG. 7I quantitative analysis of cell viability (%).

FIGS. 8A-8C: Odontogenic gene expression analysis of DPSCs culture on PDA-GICs or Fuji IX® specimens after two weeks of culturing in regular media. '25% PDA', '75% PDA', '100% PDA' means that from a total of 100% GIC particles, 25% or 75% or 100% of the particles respectively were coated with PDA. 'Fold change' refers to the amount of increase in the gene expression when there is no PDA and to the amount of increase after addition of PDA, FIG. 8A DSPP, FIG. 8B DMP-1, FIG. 8C MEPE.

Figure 1A:
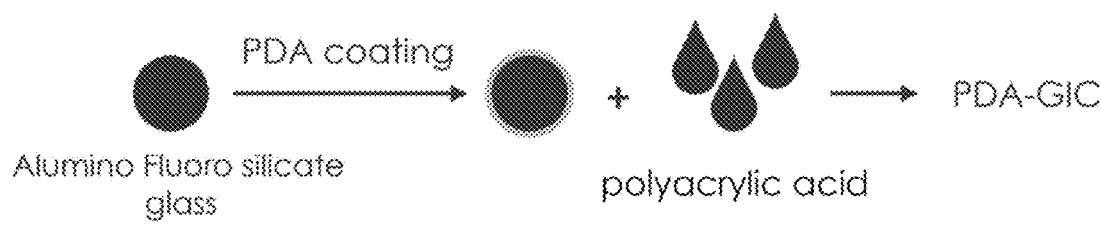
FIG. 1A shows an illustration of the fabrication of polydopamine (PDA) coated glass particles and PDA containing glass ionomer cements.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE PRESENT INVENTION

Glass ionomer cements (GIC) were invented by Wilson et al. at the Laboratory of the Government Chemist in 1969. These materials are water-based cements also known as polyalkenoate cements. They are based on the reaction between an alumino-silicate glass and polyacrylic acid, and cement formation arises from the acid-base reaction between the components. The glass ionomer name is derived from the formulation of the glass powder and the ionomer that contains carboxylic acids. These cements are adhesive to tooth structure and are translucent. The matrix of the set cement is an inorganic-organic network with a highly cross-linked structure. The first glass ionomer cement (GIC) introduced had the acronym "ASPA" and comprised alumina-silicate glass as the powder and polyacrylic acid as the liquid. This product was first sold in Europe (De Trey Company and Amalgamated Dental Company) and later in the USA. Glass ionomer cements have desirable properties, such as adhesion to moist tooth structure and an anti-cariogenic action (due to fluoride release). In addition, the coefficient of thermal expansion for glass ionomers is close to that of tooth structure and they are biocompatible. Because of these unique properties, GICs are very useful and important as dental restorative materials.

However, in addition to their advantages, GICs suffer from a number of disadvantages such as lack of remineralization properties, low bond strength to tooth structure, long setting time, brittleness, poor compressive strength and poor fracture resistance, all of which limit their utility. Therefore, there is a need to improve the biological and physical properties of glass-ionomer cements (GICs).

In the present invention, a novel bioactive dental restorative material is introduced. This new dental material is based on glass-ionomer cements with remineralization capability. Moreover, this new glass-ionomer cement formulation exhibits enhanced physical (fast setting time) and mechanical strength and enhanced adhesion to tooth structure for applications in dentistry and orthopedics.

The present invention relates to synthesis of novel polydopamine (PDA)-modified fluoroaluminosilicate glass bioceramic particles and their applications in dentistry and orthopedics. This novel glass-ionomer formulation stimulates mineral hydroxyapatite formation and the natural re-mineralization process at the cement tooth interface, induces tertiary dentin formation, reduces sensitivity, prevents secondary caries, and prevents microleakage. Additionally, due to the presence of PDA, the developed cement exhibit superior bond strength to dentin tooth structure, presents with a sharp setting time and superior mechanical properties. This novel glass-ionomer dental cement can be used as a restorative material, cavity liner, or a luting cement. Additionally, since it can regenerate a layer of hydroxyapatite on the surface of the tooth and bonds to tooth structure it can be used for direct/indirect pulp capping procedures. Finally, the PDA-modified particles in an unfilled (without any additive fillers) resin or gel can be used as over-the-counter product against enamel white spots (pre-carious lesions) and dentin sensitivity. According to this aspect and in one embodiment, the patient is able to use pre-fabricated trays containing PDA-containing gel or resin intraorally similar to a bleaching tray or a nightguard.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

In one embodiment, this invention provides a glass ionomer cement composition comprising fluoroaluminosilicate glass particles coated by polydopamine (PDA). In one embodiment, the thickness of the polydopamine coating layer ranges between 5 and 100 nanometers in thickness.

In one embodiment, the composition further comprising a fluoroaluminosilicate glass particles not coated by polydopamine. In one embodiment, the relative amount of fluoroaluminosilicate glass microparticles coated by polydopamine is from 1% to 100% of the total fluoroaluminosilicate glass microparticles present in the composition. In one embodiment, the relative amount of fluoroaluminosilicate glass microparticles coated by polydopamine in the composition is from 1% to 50%, from 1% to 95% or from 8% to 30% of the total amount of fluoroaluminosilicate glass microparticles in the composition.

In one embodiment, the composition further comprising polyacid. In one embodiment, the polyacid is selected from polyacrylic acid, itaconic acid, maleic acid, tartaric acid or any combination thereof.

In one embodiment, the composition further comprising a resin. In one embodiment, the resin is selected from HEMA (hydroxyethyl methacrylate), Bis-GMA (bisphenol A-glycidyl methacrylate), TEGMA (Triethylene glycol dimethacrylate) or UDMA (urethane di-methacrylate resin) or any combination thereof. In one embodiment, the dopamine-coated fluoroaluminosilicate glass particles are disposed within the hydroxyethyl methacrylate resin (or in any other resin). In one embodiment, the hydroxyethyl methacrylate resin (or any other resin) is light cured.

In one embodiment, the composition exhibits a setting time of less than 5 minutes at 25° C. In one embodiment, the polydopamine comprises polydopamine HCl. In one embodiment, the glass further comprises calcium, sodium or a combination thereof.

In one embodiment, this invention provides a method of using the cement composition as described herein above in dentistry, the method comprising:
    mixing the fluoroaluminosilicate glass particles coated by polydopamine (PDA) with the fluoroaluminosilicate glass particles not coated by polydopamine (PDA) to form a powder mixture;
    disposing the mixture at an in vivo site.

In one embodiment, the method further comprising:
    remove caries from a tooth;
    rinse the cavity after caries removal;
    mix the powder comprising PDA-coated glass particles with a liquid comprising polyacid;
    place the PDA-containing GIC directly in the cavity;
such that the cement composition acts as a restorative material or as a cavity liner for the tooth.

In one embodiment, the step of mixing the powder and liquid is conducted prior to, in parallel to, or following the step of rinsing the cavity after caries removal. According to this aspect and in one embodiment, a certain step in methods of this invention is performed by one professional and a different step is performed by another professional. According to this aspect and in one embodiment, certain steps of the method are conducted in parallel to other steps.

In one embodiment, rinsing the cavity is performed with water, i.e. the cavity is rinsed with water. In one embodiment, after rinsing with water, and prior to placing the PDA-containing GIC directly in the prepared cavity, the cavity is dried.

In one embodiment, rinsing the cavity is followed by drying. In one embodiment, the cavity is rinsed with water and then dried.

In one embodiment, the method of using the cement composition in dentistry further comprises:
    mixing the powder comprising PDA-coated glass particles with a liquid comprising polyacid to form a cement;
    load a crown or restoration with the cement;
    place the crown or restoration in a patient's mouth;
such that the cement composition acts as a luting element.

In one embodiment, the method of using the cement composition in dentistry further comprises:
    mixing the powder comprising PDA-coated glass particles with a liquid comprising polyacid to form a cement;
    remove caries in an incomplete manner such that a layer of affected dentine is kept.
    apply the invented cement to the dentin layer;
such that the cement composition acts as a pulp capping.

In one embodiment, the method of using the cement composition in dentistry further comprising applying the cement to a tooth such that the cement composition acts as a material to bond to carious lesions, a material to reduce teeth sensitivity, as a material to promote mineralization of teeth white spots or to any combination thereof.

In one embodiment, this invention provides a method of using the particle composition as described herein above to generate a layer of hydroxyapatite at the surface of a tooth, the method comprising:
    disposing the dopamine-coated fluoroaluminosilicate glass particles in a resin;
    applying the composition to white spots on the surface of the tooth.
    curing the composition by light irradiation.

According to this aspect and in one embodiment, the step of disposing the particles in the resin comprises disposing a powder of the particles comprising PDA-coated GIC particles in the resin. The particles are mixed with the resin in one embodiment.

In one embodiment, the method further comprising extraction of calcium and phosphate from a patient saliva by said composition and initialization of remineralization.

In one embodiment, the composition application step is being conducted by a physician or by a patient. In one embodiment, the composition in an unfilled resin is supplied as an over-the-counter (OTC) product. In one embodiment, the OTC product comprises a pre-loaded tray with PDA-coated glass-ionomer-cement particles in an unfilled resin.

In some embodiments, the step of curing by light is optional. According to this aspect and in one embodiment no light-curing is performed. For example, an OTC product does not require light curing in one embodiment, while the office version of the product is light curable in one embodiment. In other embodiments, the office preparation does not require light curing.

In embodiments of this invention, GIC compositions of the invention comprise glass particles (coated by PDA, or uncoated, or a combination thereof), acidic polymer or acidic copolymer or a combination thereof. In some embodiments, compositions of this invention comprise a resin. The weight ratio of glass particles to acidic polymer and/or to the resin when incorporated can be any ratio within a range known in the art. In one embodiment, the polyacid(s) used to form the GIC are selected from polyacrylic acid, polylactic acid, polyitaconic acid, any polyalkenoic acid, tartaric acid or any combination thereof.

In one embodiment, the powder is or comprises fluoro-alumina-silicate particles coated with PDA. In one embodiment, the liquid is or comprises a copolymer of acrylic acid and itaconic acid.

GIC of this invention are used for various applications, for example:
 a. Filling (restorative) material;
 b. Cavity liner for larger fillings;
 c. Luting cement to cement crowns and bridges or other restorations;
 d. Pulp capping material for situations where caries are very close to the pulp of the tooth;
 e. Anti-caries or anti-sensitivity agent for sensitive teeth or for teeth with hypocalcified enamel.

The invention disclosed herein has a number of embodiments. A typical embodiment of the invention is a glass ionomer cement composition comprising fluoroaluminosilicate glass particles coated by dopamine (e.g. dopamine hydrochloride), optionally in combination with fluoroaluminosilicate glass microparticles not coated by dopamine hydrochloride. In such compositions, the relative amounts of fluoroaluminosilicate glass microparticles coated by dopamine hydrochloride can be from 1% to essentially 100% of the total fluoroaluminosilicate glass microparticles present in the composition (e.g. where 1% to 50%, 1% to 95%, 1% to 100%, 5% to 95%, 5% to 100%, 8% to 30%, 30% to 80%, etc., of the fluoroaluminosilicate glass microparticles in the composition are coated by dopamine hydrochloride while the other fluoroaluminosilicate glass microparticles in the composition are not coated by polydopamine) In one embodiment, the polydopamine is coated on the fluoroaluminosilicate glass microparticles to form a layer that is between 5 and 50 nanometers in thickness. These fluoroaluminosilicate glass microparticles can form a powder component of a multi-component mixture, for example a mixture that includes this first powder component in combination with a second liquid component, for example one that includes a polyacid such as polylactic acid.

In these multicomponent glass ionomer cement compositions, the dopamine coating the fluoroaluminosilicate glass microparticles is included in amounts and disposed on the microparticles in a way that makes the composition having a number of desirable physical/material qualities. For example, in some embodiments of the invention, the composition comprising the mixture of fluoroaluminosilicate glass microparticles including particles coupled to dopamine exhibits a compressive strength that is at least 10% greater (e.g. 10%-35% greater) than the compressive strength observed with a control/comparative composition that does not comprise fluoroaluminosilicate glass microparticles coupled to dopamine hydrochloride. In some embodiments of the invention, the composition comprising the mixture of fluoroaluminosilicate glass microparticles including particles coupled to dopamine exhibits a flexural strength that is at least 10% greater (e.g. at least 2× greater) than the flexural strength observed with a control/comparative composition that does not comprise fluoroaluminosilicate glass microparticles coupled to dopamine hydrochloride. In some embodiments of the invention, the composition comprising the mixture of fluoroaluminosilicate glass microparticles including particles coupled to dopamine exhibits a shear bond strength that is at least 10% greater (e.g. at least 2× greater) than the shear bond strength observed with a control/comparative composition that does not comprise fluoroaluminosilicate glass microparticles coupled to dopamine hydrochloride. In some embodiments of the invention, the composition comprising the mixture of fluoroaluminosilicate glass microparticles including particles coupled to dopamine exhibits a hardness after 7 days that is at least 10% greater than the hardness observed with a control/comparative composition that does not comprise fluoroaluminosilicate glass microparticles coupled to dopamine hydrochloride. In some embodiments of the invention, the composition comprising the mixture of fluoroaluminosilicate glass microparticles including particles coupled to dopamine exhibits an adhesion to dentin (bonding to substrate) that is at least 2× the adhesion observed with a control/comparative composition that does not comprise dopamine hydrochloride.

In some embodiments of the invention the compositions of the invention facilitate hydroxyapatite remineralization, for example so that after 7 days following application of the composition to a surface of a tooth, hydroxyapatite remineralization is observed. Typically, this hydroxyapatite remineralization is at least 10% (e.g. at least 100%) greater than hydroxyapatite remineralization observed with a control/comparative composition that does not comprise dopamine hydrochloride. In some embodiments of the invention, the compositions of the invention are disposed within a hydroxyethyl methacrylate resin that is curable with light. In certain embodiments of the invention, the composition exhibits a setting time of less than 5 minutes at 25° C.

Embodiments of the invention include methods of using the compositions of the invention, for example as a restorative material, a cavity liner, as a luting cement, for pulp capping, as a material to bond to carious lesions, as a material to reduce teeth sensitivity; or as a material to promote mineralization of teeth white spots. In these embodiments, the methods comprising mixing together the powder and liquid glass-ionomer-cement components and then disposing this mixture at an in vivo site where the glass ionomer cement acts as a dental or bone restorative material/cement; a cavity liner; a luting cement; a pulp capping cement; a material to bond to carious lesions; a material to reduce teeth sensitivity; or a material to promote mineralization in vivo (e.g. of teeth white spots). In certain embodiments of the invention, the compositions of the invention are used to generate a layer of hydroxyapatite at the surface of a tooth, wherein after 7 days, hydroxyapatite remineralization is at least 10% (e.g. at least 100%) greater than hydroxyapatite remineralization observed with a control/comparative composition that does not comprise dopamine hydrochloride.

In one embodiment, this invention relates to dental adhesive hydrogel compositions and methods for making and using them.

Without being bound to any theory, it is believed that the hydroxyl and the amine groups in the PDA coating interact with the acid, leading to increased acid-base reaction and increase in the mechanical properties of the GIC in some embodiments.

A major advantage of using a resin in compositions of this invention is that it makes it visible light crosslinkable. Any photocrosslinkable resin can be used in embodiments of this invention, such as Bis-GMA (bisphenol A-glycidyl methacrylate), TEGMA (Triethylene glycol dimethacrylate), UDMA (urethane di-methacylate resin), or HEMA (hydroxyethyl methacrylate).

In one embodiment, when the particle composition is incorporated in a resin, light is applied to the composition/resin after incorporation, for resin cross linking. The resin comprising the composition can be exposed to a 'blue light' lamp. The resin comprising the composition can be cured by any electromagnetic irradiation source. The curing wavelength of the irradiation source is chosen to fit the specific resin employed. The curing wavelengths for each resin/polymer are known in the art. The curing wavelength can be in the UV range, in the visible range or in other spectral ranges as required by a certain resin. Crosslinkable means that the resin is capable of forming cross-linkages (capable of becoming cross-linked) upon exposure to light/irradiation.

In one embodiment, acid-base reaction triggers setting of the cement. Acid is provided by the polyacid in the liquid and the base is the glass in the glass particles in one embodiment.

In embodiments of this invention, the cement composition acts as a restorative material, a cavity liner, a luting cement, a pulp capping, material to bond to carious lesions, a material to reduce teeth sensitivity, as a material to promote mineralization of teeth white spots or as any combination thereof.

In embodiments of this invention, wherein the cement composition acts as a restorative material or cavity liner, the clinician prepares the cavity after caries removal and places the PDA-containing glass ionomer (after mixing the powder and liquid) directly in the prepared cavity. When used as a luting cement, the clinician loads the crown or restoration with the invented cement and places the restoration in a patient's mouth. As a pulp capping material, the invented cement is used in instances when complete caries removal will expose the pulp (nerve) of the tooth. In this situation, the clinician keeps a layer of affected dentine and applies the invented cement on it. In all these situations, no additional material is necessary. The procedures are done at body temperature.

In some embodiments, this invention provides a method of using GIC compositions of this invention to generate a layer of hydroxyapatite at the surface of a tooth, the method comprising applying the composition to a surface of a tooth.

In some embodiments, this technique is used for treatment of incipient caries (white spots) on tooth structure. White spots are hypocalcified structures that are not decayed yet. According to this aspect and in one embodiment, a layer of the PDA-coated glass ionomer cements in an unfilled resin is coated on the surface of the tooth and is then light-cured. The invented material extracts calcium and phosphate from the patient's saliva and start remineralization. This technique can be done by the patient himself as well via using an OTC product (a pre-loaded tray with PDA coated glass ionomer cement particles in an unfilled resin).

Particles coated by PDA are sometimes refer to as particles coupled to PDA. In embodiments of this invention, particles are fully-coated by PDA. In other embodiments, particles are partially coated by PDA. In embodiments, clusters or aggregates of particles are coated (fully or partially) by PDA. Embodiments of this of this invention includes collections of particles coated by PDA wherein the particles are fully coated, partially coated or wherein some particles are fully coated while others are partially coated. All such combinations in some embodiments, are mixed with particles that are not coated by PDA, to form compositions of particles of this invention. In other embodiments, the PDA coated particles (fully or partially or combinations thereof) are used in compositions of this invention without additional non-PDA-coated particles. According to this aspect and in one embodiment, the collection of coated particles (partially or fully or partially and fully) is not mixed with a collection of non-coated particles before mixing with the liquid acid.

In some embodiments, the glass particles used are FAS, or comprise FAS. FAS is fluoroaluminosilicate. Other glasses may be used, e.g. glasses that do not comprise fluoride and/or aluminum ions or glasses that comprise any ion/atom combination of calcium, sodium, phosphorous, fluoride, aluminum, iron, silicon. Embodiments described herein for FAS are applicable to any other glass from the glasses described herein above.

GIC refers to glass ionomer cement. The term 'ionomer' relates to the polyacid used to form the cement. However, the glass particles are also referred to as 'GIC particles' as known in the art and in view of their use in the formation of GIC cement. Accordingly, 'PDA coated glass particles' are referred to as 'PDA coated glass ionomer particles' or 'PDA coated GIC particles' in some embodiments and the terms are interchanged. Similarly, the term 'cement composition' is sometimes used for particle compositions that do not include the liquid acid. Similarly, 'glass powder' is sometimes referred to as 'glass ionomer powder' in view of it's use in forming the glass ionomer cement.

In some embodiments, for cement preparation, specific scoops were used for the powder and one drop of liquid has been added. A powder/liquid (P/L) ratio of 3.6/1 was obtained.

In some embodiments, molded specimens were prepared from cement paste. According to this aspect and in one embodiment, after mixing the particle powder and the acidic liquid, while the mixture is in a paste condition, the specimens were prepared by pouring the paste in the related molds.

According to this aspect and in one embodiment, the mixed powder and liquid forms a paste. After a period of time, the paste sets and becomes hard.

Particles of this invention can be of any diameter (or other dimension) range(s) from nanometers (nm) to millimeters (mm). In some embodiments, particles of this invention are microparticles (particles with micron-sized diameter). In some embodiments, collections of glass particles used in this invention (before application of PDA-coating) comprise microparticles, nanoparticles or any combination thereof. In some embodiments microparticles are particles with a diameter ranging between 1 micron and 1000 micron. Powders or collection of particles of this invention may be monodispersed (i.e. comprise particles of the same or of similar size, i.e. the particle collection is of narrow size-distribution) or it may comprise particles with large size distribution. Embodiments that are described herein for microparticles are also applicable to particles of other dimensions.

The thickness of the PDA coating on particles of this invention ranges from 5 nm to 50 nm in one embodiment. In other embodiments, PDA coating thickness ranges from 1 nm to 100 nm, 5 nm to 100 nm, 1 nm to 1 micron, 1 nm to 100 microns. Any other coating thickness that is suitable for GIC applications is included in embodiments of this invention.

In some embodiments, coating of the particles is complete. In some embodiments the particles are fully-coated by the PDA. In other embodiments, the particles are partially-coated by the PDA. In some embodiments, the particles are more than 50% coated. In other embodiments, the particles are less than 50% coated by PDA. Collections of particles used in this invention may include fully coated particles, partially coated particles or any combination thereof.

In some embodiments, procedures used for making the innovative cements of this invention include mixing the particle powder with acidic liquid and allowing the formed mixture to set and harden.

Powder/PDA mixing times, powder/acidic-liquid mixing times, liquid compositions, powder to liquid ratio, powder to resin ration, resin compositions, acid liquid composition, setting times and mixing/setting temperatures are not restricted to a certain value. Such parameters may vary and can be chosen or set to any value as known in the art of glass/resin and of glass-ionomer cements. For example, and in one embodiment, mixing or working time of the glass particle powder and the liquid comprising the acid is 1 minute or 2 minutes or 3 minutes or it ranges between 10 sec and 10 min or between 1 min and 5 min or between 1 min and 7 min in some embodiments. Curing/setting time is 1 minute or 2 minutes or 3 minutes in some embodiments or it ranges between 10 sec and 10 min or between 1 min and 5 min or between 1 min and 7 min in some embodiments.

In some embodiments, the powder includes dry polyacid as well.

In one embodiment, the PDA-coated glass ionomer particles were mixed with a liquid comprising polyacrylic acid at a 3.6/1 powder to liquid ratio by weight (g/g).

In one embodiment, two components are described for the cement formation:
Component 1: the GIC dry powder (coated/uncoated particles)
Component 2: the liquid comprising the acid.
In embodiments described herein these two components are described.

In some embodiments, the liquid comprises the acid. In one embodiment, the liquid comprises polyacid dissolved in water. The molecular weight of the polyacid used may vary and can be chosen to be suitable for an appropriate cement preparation.

In one embodiment, 'component 1', in addition to the glass particles comprises dry acid (polyacid). According to this aspect and in one embodiment, the glass particles/dry acid are mixed with a liquid that comprise acid in one embodiment or with a liquid that does not comprise acid in another embodiment. In some embodiments, the glass-ionomer cement is referred to as glass-ionomer material.

In one embodiment, this invention provides a powder, said powder comprising glass particles coated by polydopamine (PDA). In some embodiments, the glass is or comprises silica. In some embodiment, the glass comprises aluminosilicate. In one embodiment, the glass comprises fluoroaluminosilicate (FAS). In some embodiments, the powder comprises glass particles that are fully-coated by PDA, particles that are partially coated by PDA, particles that are not coated by PDA or any combination thereof. Powder is also referred to as a collection of particles in embodiments of this invention.

In some embodiments, this invention comprises a kit for the preparation of glass ionomer cement of the invention. In some embodiments, the kit comprises two vessels (containers). A first container comprises PDA-coated particles and a second container comprises a liquid, the liquid comprising polyacid.

In one embodiment, the first vessel that comprises a powder, comprises PDA-coated particles. In one embodiment, the powder comprises glass particles that are fully-coated by PDA, particles that are partially coated by PDA, particles that are not coated by PDA or any combination thereof in which at least some particles are partially or fully coated by PDA.

In some embodiments, the kit further comprises one or more of: liquid dispensing tools or elements, powder measuring tools or elements, a surface on which mixing can take place, mixing bowl/container, support for the containers, mixing tools or elements. In some embodiments, the liquid dispensing tool and/or the powder measuring tool is/are associated with the relevant containers, e.g. the liquid container is a squeeze bottle from which drops of liquid are dispensed in a controlled manner Another example is a container for the powder, in which the cap/lid of the container serves as the powder measuring tool.

In some embodiments, kits of this invention comprise a container comprising a resin. According to this aspect and in one embodiment, measuring/dispensing tools/elements are included in the kit for measuring/dispensing the resin.

In one embodiment, this invention provides a glass particle coated by PDA. In one embodiment, this invention provides a glass particle coated by polydopamine (PDA), wherein the thickness of the PDA coating ranges between 1 nm and 100 nm or between 5 nm and 50 nm in some embodiments.

For many uses as described herein above, cement preparation and use is conducted at room temperature. However, it is to be noted that cement formation/preparation and cement use can be done at other temperatures, higher or lower than room temperature. Room temperature is usually around 18-25° C. but can be defined as any temperature between 20-30° C., 10-30° C., 0-40° C., (−10)-40° C. etc.

In one embodiment, glass particles of this invention are ball-shaped or circular shaped and their size is defined by their diameter. However, particles in powders of this invention can be of any shape including rod-like particles, other elongated particles, non-symmetric ball-shaped particles, polyhedral, rectangular, cube-shaped, oval-shaped, or particles of any other form, including symmetric, non-symmetric or partially symmetric particles, particles with smooth surface, particles with rough surface or any combination thereof.

In one embodiment, this invention provides a process for making polydopamine-coated fluoro aluminate silicate (FAS) glass ionomer particles.

In one embodiment, the process comprising:
dispersing glass particles in a buffer;
optionally ultrasonicating the dispersion;
adding dopamine hydrochloride to the dispersion;
stirring the dispersion;
collecting the particles from the dispersion;
optionally washing the particles;
optionally drying the particles.

In one embodiment, the buffer is mM tris(hydroxymethyl) aminomethane (TRIS) buffer. In one embodiment, the pH of the buffer is (pH=8.5). In one embodiment, the dispersion is formed or the formation of the dispersion is facilitated by the use of vortexing. In one embodiment, ultrasonication is conducted at room temperature. In one embodiment, ultrasonication is used for 10 min or from 30 sec to 20 min. In one embodiment, stirring is applied for 4-16 h or for 1 h to 24 h. In one embodiment, stirring is conducted at room temperature. In one embodiment, stirring is conducted in the dark. In one embodiment, particles were collected by centrifugation. In one embodiment, centrifugation is performed at 300×g for 5 min. In one embodiment, the collected particles are washed with distilled water. In one embodiment, the collected particles are washed triple times with milli-Q® water (>15 MΩ). In one embodiment, the collected particles are dried at a vacuum oven. In one embodiment, in the process for making polydopamine-coated glass ionomer particles, the weight ratio of glass particles to dopamine that are mixed to form the coated particles is 10:1, 20:1, 1:1. In one embodiment, the glass particles to DPA (glass:DPA) weight ratio in preparations for producing PDA coated particles, ranges between 20:1 and 1:20, between 1:1 and 100:1, between 50:1 and 10:1. Between 100:1 and 1:1 between 1000:1 and 1:1 between 1000:1 and 1:10 between 10,000:1 and 1:1, between 20:1 and 1:1 between 50:1 and 1:1.

In one embodiment, this invention provides a method of using the cement compositions of this invention in dentistry. According to this aspect and in one embodiment, the method comprising mixing the glass particles coated by polydopamine (PDA) with glass particles not coated by polydopamine (PDA) to form a powder mixture. The powder mixture is then mixed with a liquid comprising a polyacid, the so formed mixture is then disposed at an in vivo site.

According to this aspect, the mixture formed from the glass particles (coated, uncoated or both) and the liquid comprising the acid is in the form of a paste. In one embodiment, this mixture is initially in the form of a paste and when it hardens it is in the form of a solid or in the form of a hardened paste. In one embodiment, the mixture is in the form of a gel.

In one embodiment when referring to particles or to powder of particles that are/is mixed with a liquid to form a cement, the liquid is a liquid comprising an ionomer, a liquid comprising an acid, a liquid comprising a polyacid, a liquid comprising a polyacid that is an ionomer. In other embodiments, the liquid does not comprise an acid, a polyacid or an ionomer.

In some embodiments, use of particles or powders of this invention for dentistry does not require mixing of the particles with any liquid.

In some embodiments, particle compositions of this invention are mixed with a liquid to form cements. In some embodiments, particle compositions of this invention are incorporated in a resin.

In some embodiments, the particles, compositions and methods described herein above for dentistry are applied to other applications such as orthopedic applications (e.g. as a bone cement for expedited fracture healing and bone regeneration/repair for skeletal defects). In some embodiments, the glass ionomer cement of this invention acts as a bone restorative material/cement. In one embodiment, powders, compositions and particles of this invention provides a new class of materials used as bone restorative material.

EXAMPLES

Example 1

Materials and Methods

In all these experiments, the invented restorative material was compared to Fuji IX GP® (commercially available GIC), which is the gold standard glass-ionomer restorative cement used routinely in everyday dental practices. The commercially available GIC particles were used for the process of coating by PDA. Following the PDA coating process, the coated particles (or coated and uncoated particles) were mixed with the Fuji IX GP® liquid to form the cement.

Example 2

Fabrication of Polydopamine (PDA) Coated Glass-Ionomer Particles

To make polydopamine-coated fluoro aluminate silicate (FAS) glass ionomer particles, 100 mg of glass ionomer particles were dispersed in 50 ml of mM tris(hydroxymethyl)aminomethane (TRIS) buffer (pH=8.5) using vertexing for 2 min followed by ultrasonication at room temperature for 10 min After adding the appropriate amount of dopamine hydrochloride (10-100 mg), the mixture was stirred for 4-16 h at room temperature in dark. Time of mixing and initial dopamine concentration together control the deposition amount and coating thickness. Particles were collected by centrifugation at 300×g for 5 min and washed triple times with milli-Q® water (>15 MΩ) and dried at vacuum oven. The formation of the PDA coating on FAS particles was confirmed by XPS (see below).

Figure 1B:
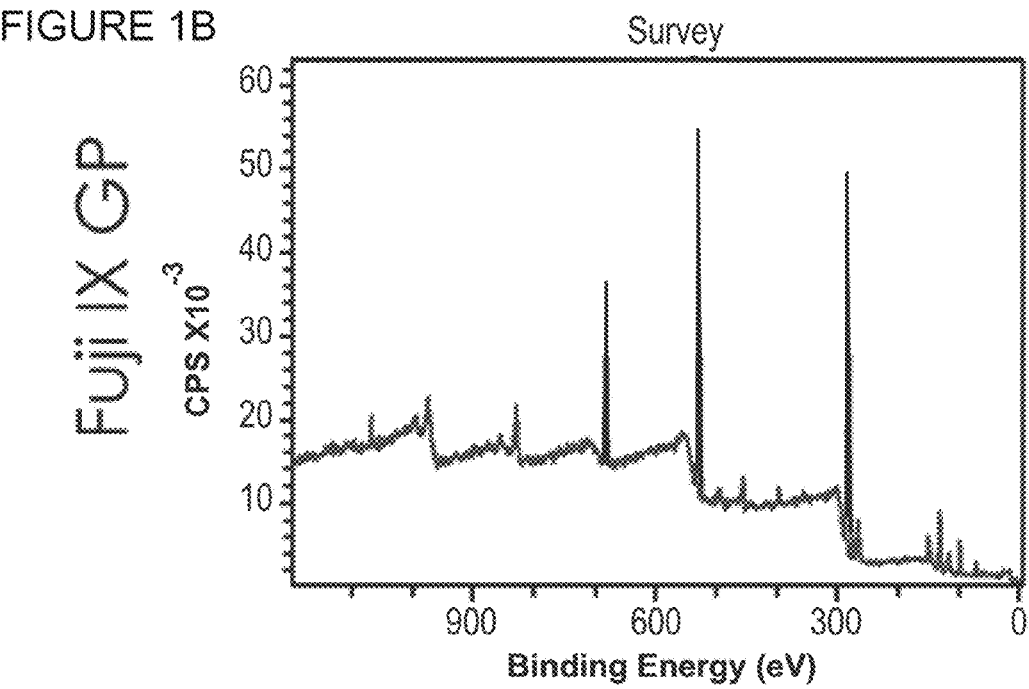
FIG. 1B shows a survey XPS analysis of a sample comprising Fuji IX GP.
Figure 1C:
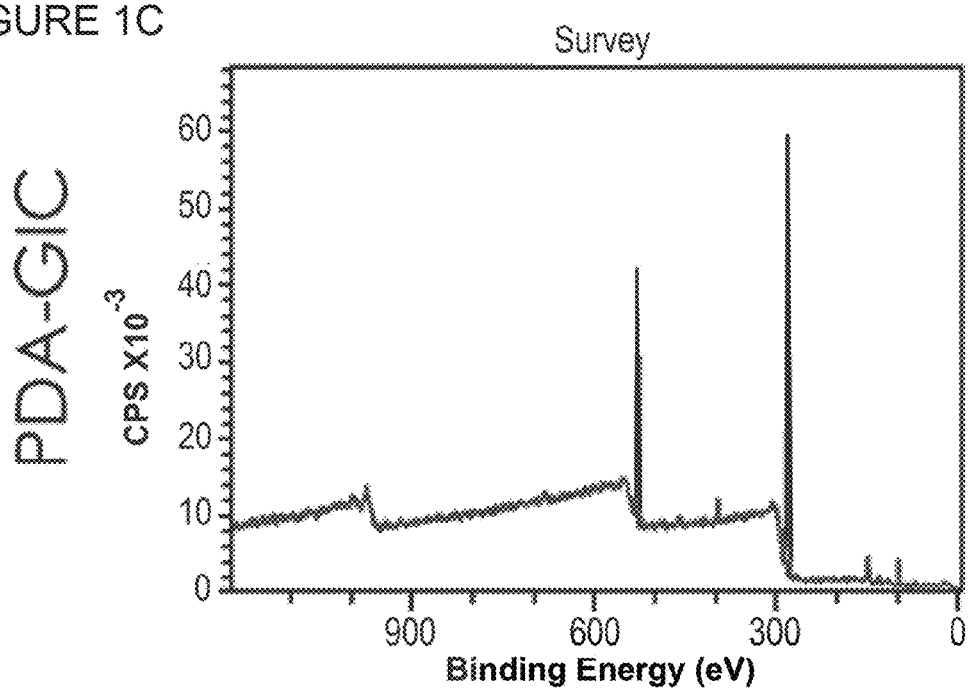
FIG. 1C shows a survey XPS analysis of a sample comprising PDA-GIC.
Figure 2A:
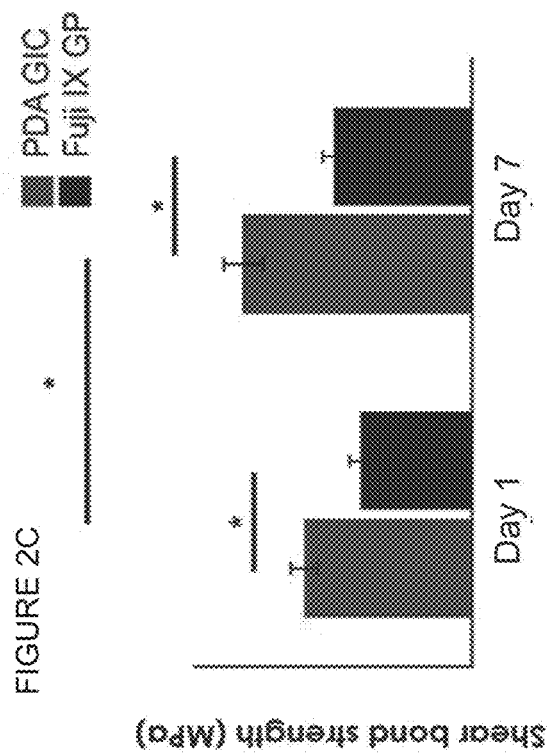
FIGS. 2A-2G: Comparative analysis of the mechanical properties of the novel PDA containing GIC in comparison to a gold standard commercially available glass ionomer restorative material (Fuji IXGP®)
Figure 2C:
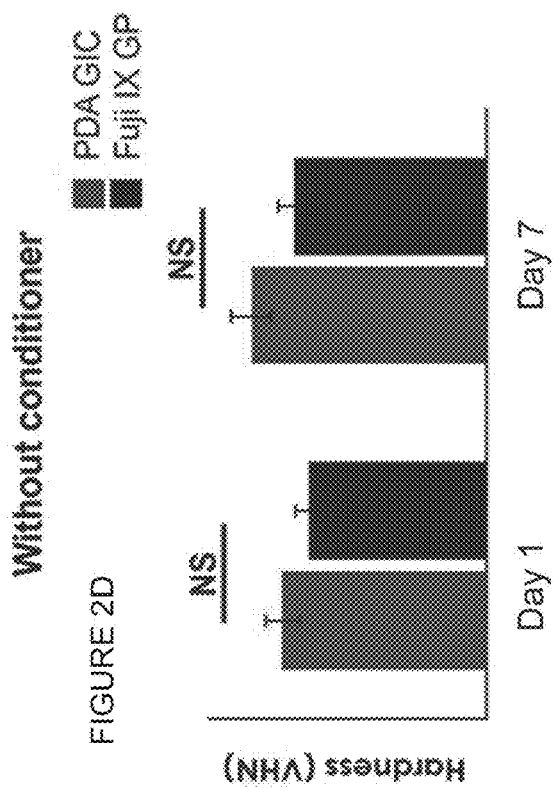
Figure 2B:
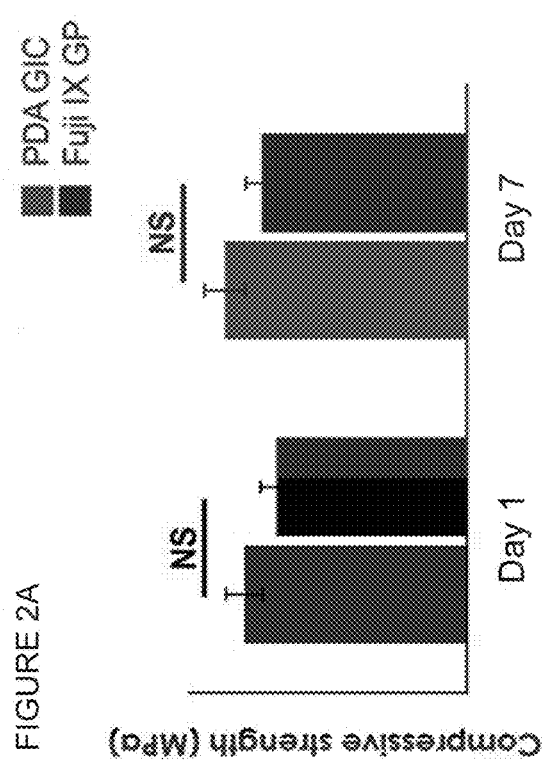
Figure 2D:
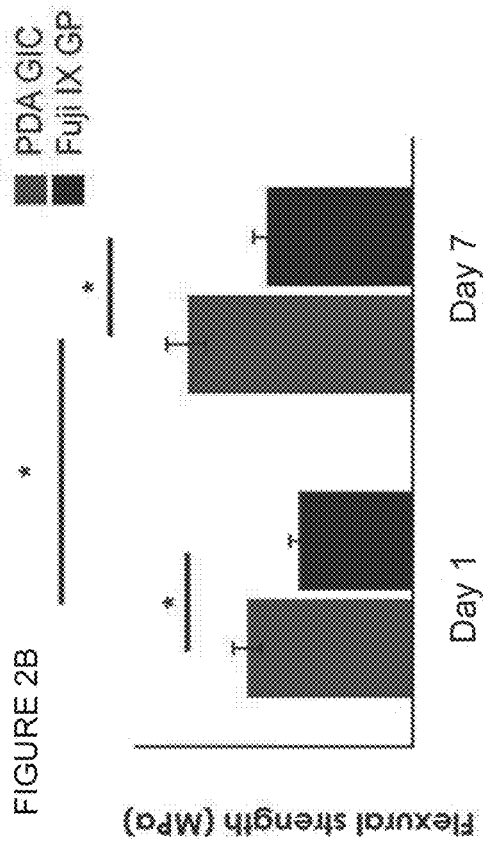
Figure 2:
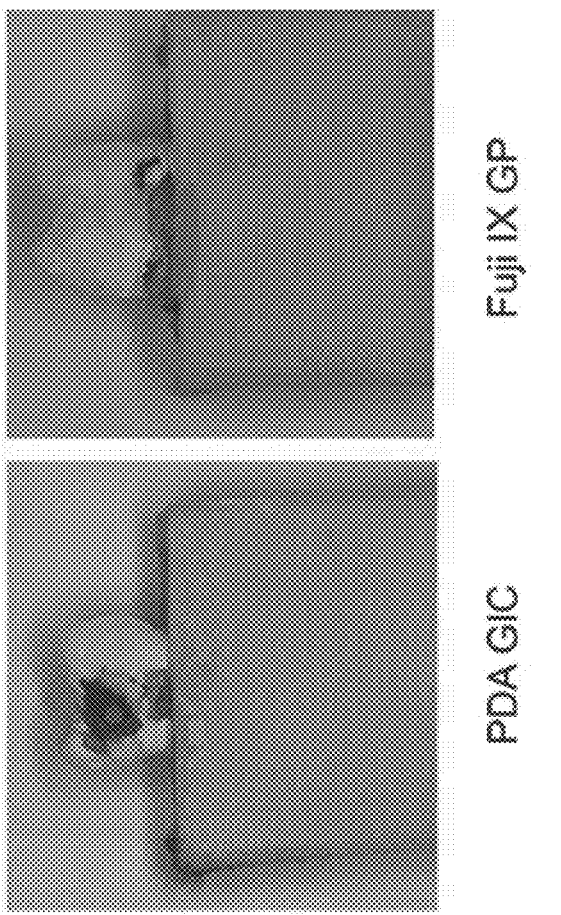
Figure 3A:
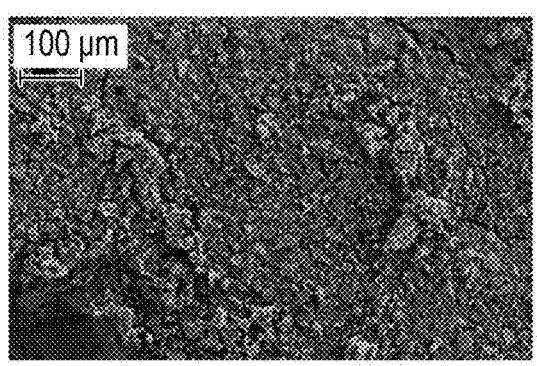
FIGS. 3A and 3B: Confirmation of the re-mineralization power of the invented PDA containing glass ionomer material. After 1 and 7 days of immersing in artificial saliva, significant amounts of mineralization was observed on the surface of the invented material. Note the start of mineralization shown by white arrows at day 1 which lead to significant amounts of mineralization at day 7. However, no mineralization was observed for the control group (Fuji IX GP®, see FIGS. 3K-3L)
Figure 3B:
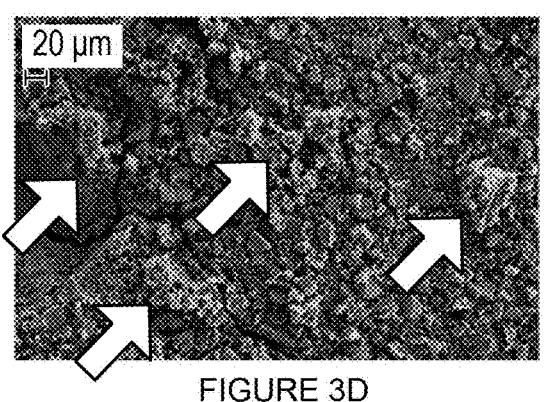
Figure 3C:
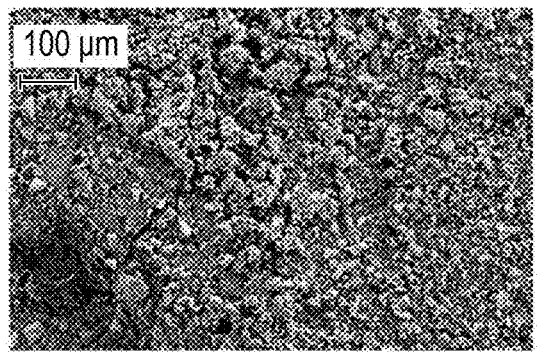
FIG. 3C PDA-GIC 7 days scale bar=100 µm.
Figure 3D:
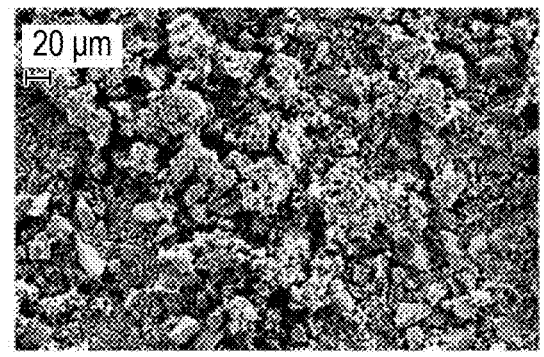
FIG. 3D PDA-GIC 7 days scale bar=20 µm.
Figure 3E:
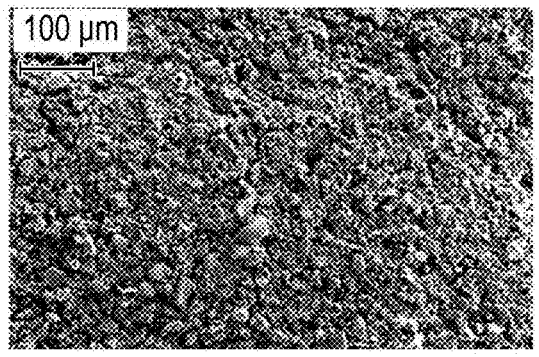
FIG. 3E Fuji IX GIC 7 days scale bar=100 µm.
Figure 3F:
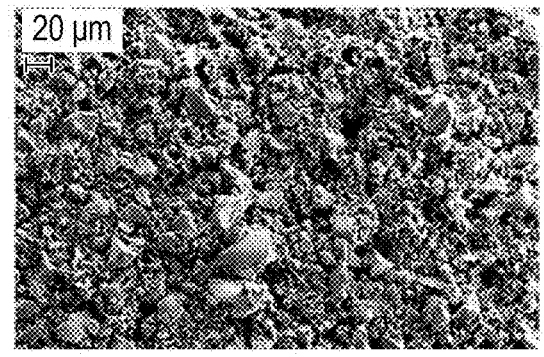
FIG. 3F Fuji IX GIC 7 days scale bar=20 µm.
Figure 3G:
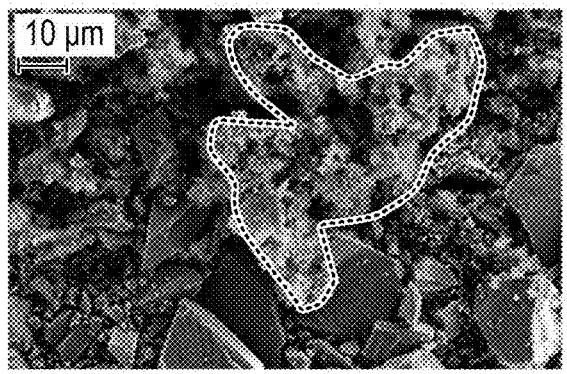
FIG. 3G PDA-GIC 1 day scale bar=10 µm; FIG.
Figure 3H:
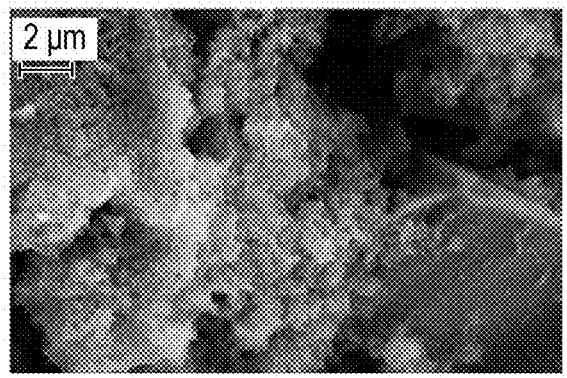
FIG. 3I PDA-GIC 7 days scale bar=10 µm.
FIG. 3J PDA-GIC 7 days scale bar=2 µm.
FIG. 3K Fuji IX GIC 7 days scale bar=10 µm.
FIG. 3L Fuji IX GIC 7 days scale bar=2 µm; FTIR analysis (FIG. 3M) confirming the presence of mineralized tissue with hydroxyapatite related peaks on the surface of the invented glass ionomer, while the control group shows only peaks related to set cement.
FIG. 3N. Semi-quantitative analysis of the mineralization area based on FIGS. 3A-3F and on FIGS. 3G-L. ***p<0.001. SEM images EHT=10.00 kV.
Figure 3I:
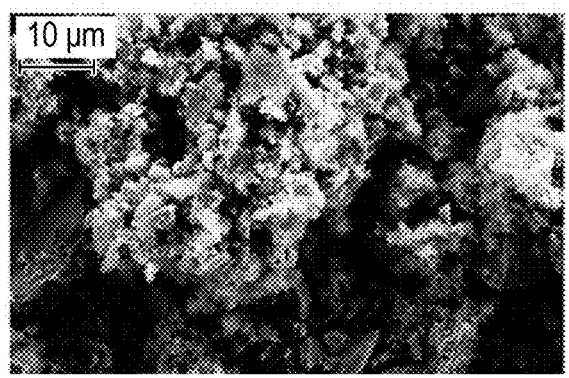
Figure 3J:
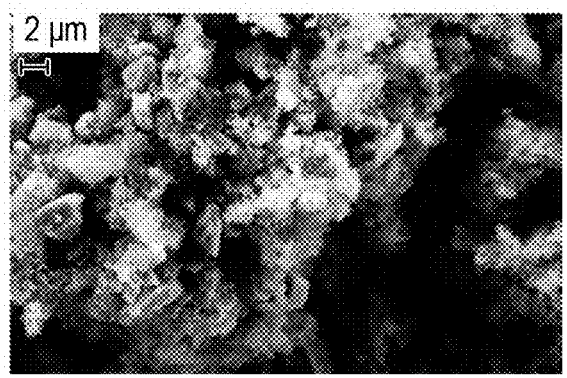
Figure 3K:
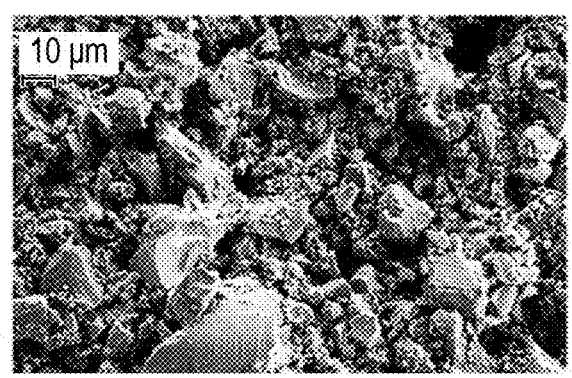
Figure 3L:
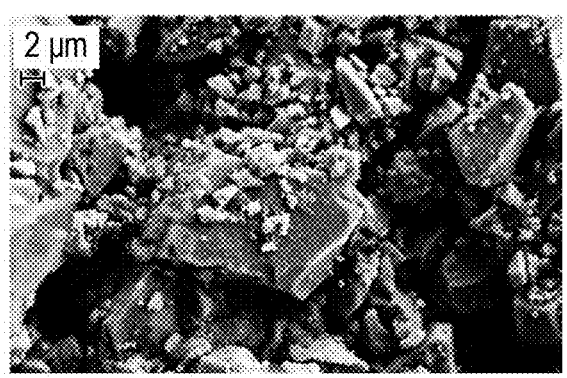
Figure 3M:
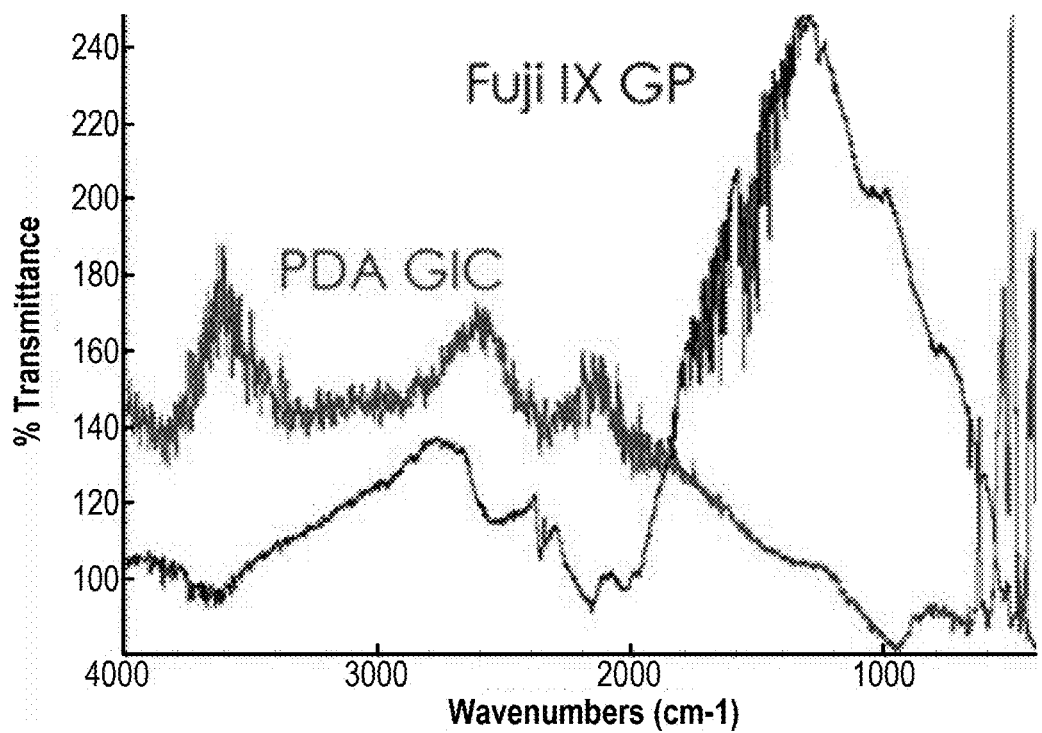
Figure 3N:
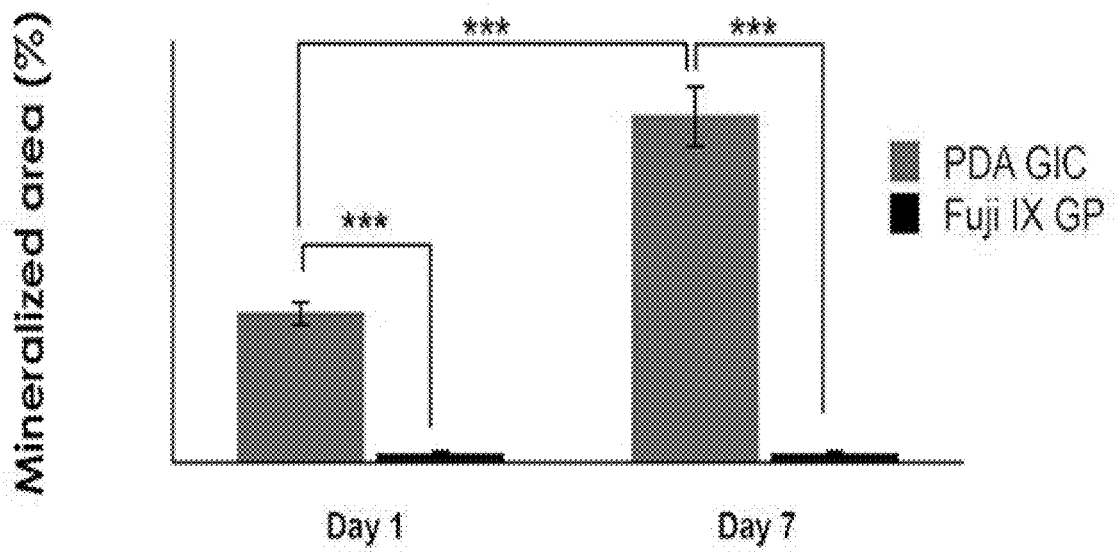
Figure 4B:
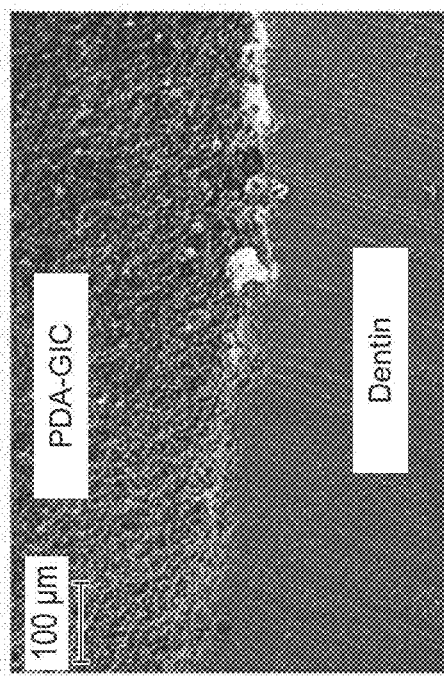
FIGS. 4A-4D (images of PDA-GIC on dentin, scale bar FIG. 4A and FIG. 4B is 100 µm, scale bar FIG. 4C is 20 µm, scale bar FIG. 4D is 10 µm) and FIGS. 4E-4H (scale bar FIG. 4E is 100 µm and FIG. 4F is 30 µm, scale bar FIG. 4G is 20 µm, scale bar FIG. 4H is 10 µm), the invented PDA-containing glass ionomer has the ability to remineralize at the interface of the decayed dentin structure. It is also capable of sealing the dentinal tubules (white arrows), which will help to decease the sensitivity and dentine regeneration at the interface of the material and the tooth structure. However, this phenomenon was not observed for the control group (FIGS. 4I-4K, FIG. 4I scale bar is 100 µm, FIG. 4J scale bar is 30 µm, FIG. 4K scale bar is 20 µm).
Figure 4D:
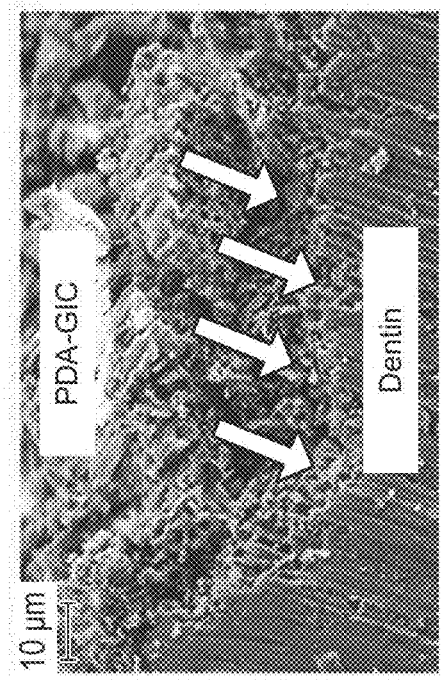
Figure 4A:
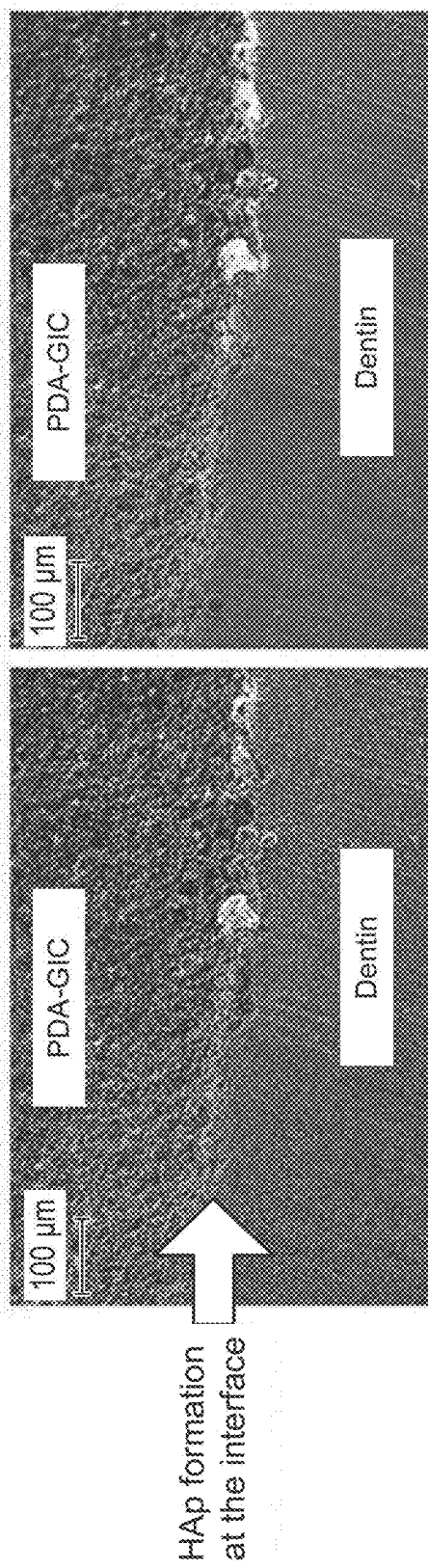
Figure 4C:
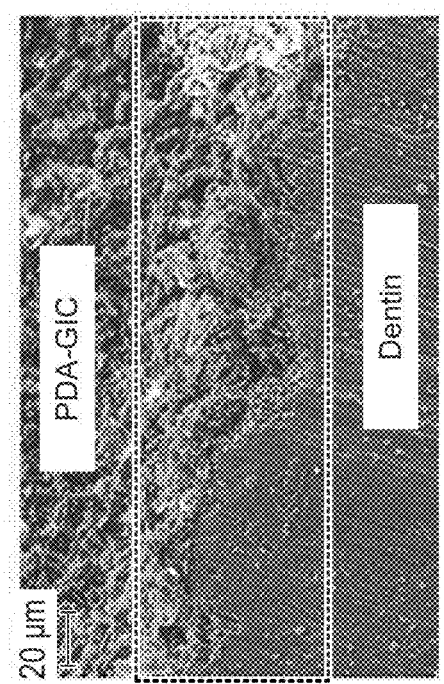
Figure 4E:
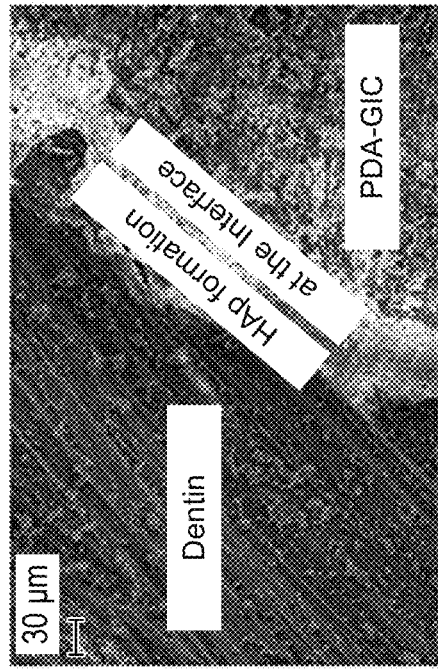
FIG. 4L shows the structure of the decayed dentine without any restorative material for comparison. The data was observed after 7 days of immersion in the artificial saliva solution at 37° C. SEM images EHT=10.00 kV.
Figure 4F:
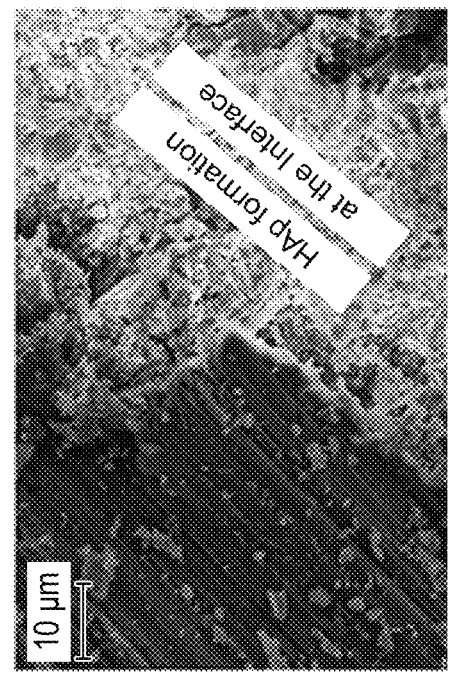
Figure 4G:
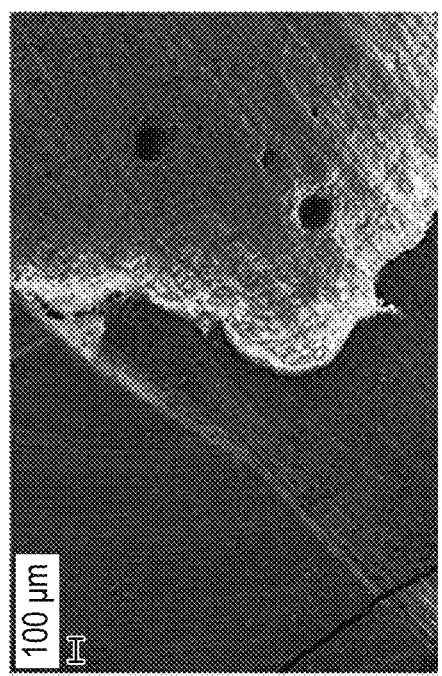
Figure 4H:
Figure 4L:
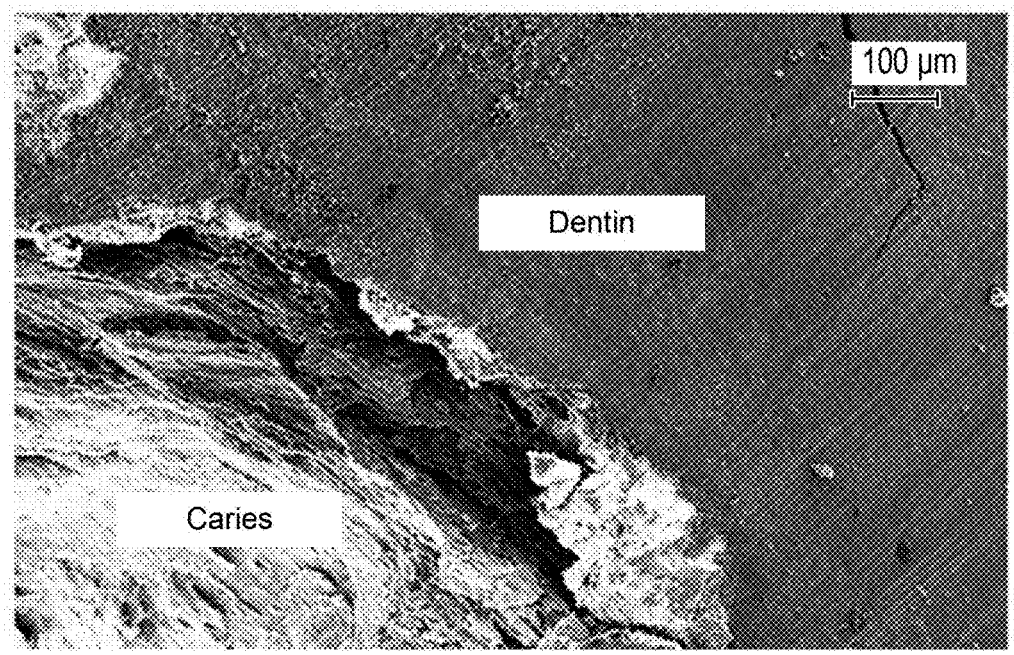
Figure 6B:
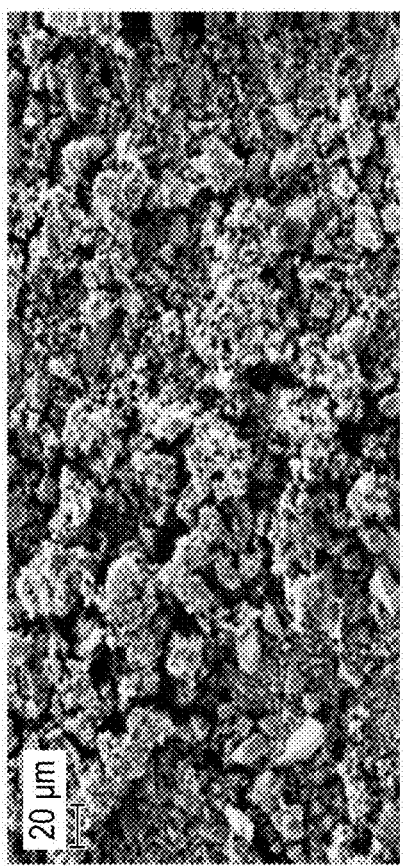
FIGS. 6A-6B: Comparison of the novel PDA-modified GIC (FIG. 6B) in comparison to the unmodified GIC (control, FIG. 6A) after 1 week in artificial saliva solution. The SEM analysis shows presence of hydroxyapatite deposition on the surface of DPA-containing GIC. Results were confirmed with XRD and EDX. Confirming the bioactivity and re-mineralization capability and potential of the novel cement. SEM images EHT=10.00 kV.
Figure 6A:
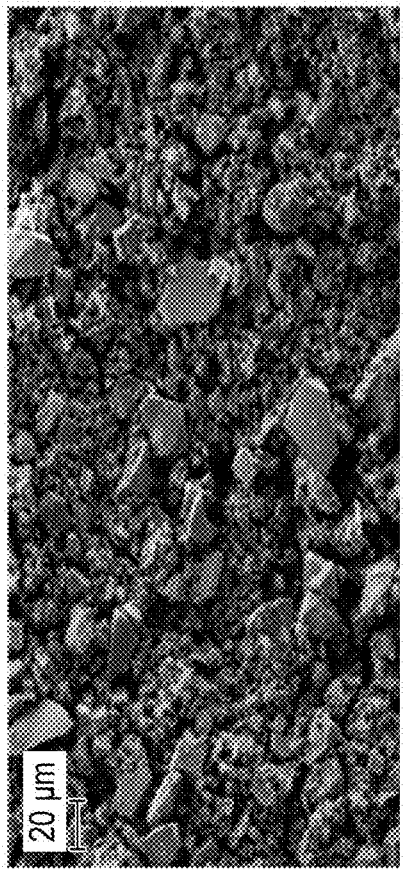

XPS Survey data in FIG. 1B and in FIG. 1C were as follows:

TABLE 1

| FUJI IX GP ® (FIG. 1B) | | | | |
| --- | --- | --- | --- | --- |
| Name | Pos. | FWHM | Area | At % |
| O 1s | 527.91 | 3.29 | 24573.88 | 20.54 |
| C 1s | 280.91 | 2.60 | 25619.49 | 62.73 |
| N 1s | 395.91 | 1.98 | 604.18 | 0.82 |
| F 1s | 680.91 | 2.75 | 10351.05 | 5.72 |
| Na 1s | 1067.91 | 2.41 | 1636.03 | 0.47 |
| Si 2p | 97.91 | 2.56 | 1921.58 | 5.76 |
| Al 2p | 70.91 | 2.60 | 869.21 | 3.96 |

TABLE 2

| PDA-GIC (FIG. 1C) | | | | |
| --- | --- | --- | --- | --- |
| Name | Pos. | FWHM | Area | At % |
| O 1s | 527.91 | 3.21 | 17978.81 | 15.47 |
| C 1s | 280.91 | 2.56 | 30220.25 | 76.18 |
| N 1s | 394.91 | 2.42 | 1287.80 | 1.80 |

TABLE 2-continued

PDA-GIC (FIG. 1C)

| Name | Pos. | FWHM | Area | At % |
|---|---|---|---|---|
| Si 2p | 97.91 | 2.44 | 1718.84 | 5.30 |
| Al 2p | 68.91 | 2.76 | 265.03 | 1.24 |

As shown above, XPS confirmed the presence of PDA coating. AFM was used for measuring the thickness of the PDA layer on the particles. PDA content per mg of GIC powder was evaluated using BCA assay.

Example 3

Mineralization Capacity of PDA Containing Glass Ionomer Cements

To study whether the developed glass ionomer cement has mineralization capacity, disc shaped PDA containing glass ionomer samples with 10 mm diameter and 1 mm thickness were prepared. The particles were coated by PDA as described in Example 2 herein above. The coated particles were then mixed with the polyacid (liquid). Powder/liquid ratio was 3.6/1. Five minutes after setting, the samples were immersed in simulated body fluid (SBF) or artificial saliva solutions (0.2 mM $MgCl_2$, 1 mM $CaCl_2$ $H_2O$, 20 mM HEPES buffer, 4 mM $KH_2PO_4$, 16 mM KCl, 4.5 mM $NH_4Cl$, 300 p.p.m. NaF, pH 7.0, adjusted with 1 M NaOH) at 37° C. for 1 and 7 days. The mineral deposition on the surface of the samples was analyzed using SEM, EDX, and FTIR (see FIG. 3A-FIG. 3N, FIG. 6A-FIG. 6B).

Example 4

Remineralization Properties Analysis

Tooth slice preparation Human third molars (extracted following the standard procedures for extraction) with and without caries were selected. Slices 0.1-0.2 cm thick were cut longitudinally using a water-cooled low speed diamond saw. To simulate early caries lesions tooth slices were acid etched with 30% phosphoric acid for 30 s and rinsed with deionized water.

The PDA coated glass ionomer particles were mixed with polyacrylic acid at a 3.6/1 powder to liquid ratio. The polyacrylic acid used had 55 kDa molecular weight. The powder and the liquid were mixed for 30-45 seconds and the material was allowed to set.

The PDA coated particles were applied on the surface of teeth with and without carious lesions. The tooth slices/PDA containing GIC were then immersed in 30 ml of artificial saliva (AS) solution (0.2 mM $MgCl_2$, 1 mM $CaCl_2$ $H_2O$, 20 mM HEPES buffer, 4 mM $KH_2PO_4$, 16 mM KCl, 4.5 mM $NH_4Cl$, 300 p.p.m. NaF, pH 7.0, adjusted with 1 M NaOH) at 37° C. for 1 and 7 days. After the allotted time the tooth slice was removed from the solution, rinsed with running deionized water for 50 s and air dried. Rinsing does not remove the GIC from the tooth and it remains bonded to the tooth structure. SEM analysis was utilized to study the remineralization capacity of the experimental glass ionomer (PDA containing GIC) in comparison to Fuji IX® as a control group (see FIGS. 4A-4L).

Example 5

Mechanical Properties Measurement

In order to prepare PDA-containing glass powders, an appropriate amount (glass powder/PDA ratio of 20:1 by wt.) of glass ionomer powder, and PDA was accurately weighed, and glass ionomer particles were surface coated by stirring GIC powder in PDA solution overnight. The glass powder was Fuji IX® GIC (GC).

The PDA-coated particles (powder) were mixed with acidic liquid. A powder/liquid (P/L) ratio of 3.6/1 was used to make the set cement as recommended by the manufacturer for the uncoated GIC. The GIC specimens were mixed and fabricated at room temperature according to the manufacturer's instructions.

The powder was measured using a measuring scoop and one drop of liquid (p/l ration: 3.6/1) has been added to the powder on a mixing pad. The powder and liquid were mixed for 30 seconds and the formed paste was added to the molds until the cement was set and hard.

Cylindrical specimens were prepared using cylindrical shaped molds 4 nm in diameter and 6 mm in height for compressive strength test. For the flexural strength test, cylindrical molds with 2 mm thickness, 10 mm length, and 2 mm height were used in order to prepare disc shaped samples with 10 mm diameter and 1 mm thickness. The molds were filled with the material and covered with a tape and glass slides, flattened and gently pressed by hand in order to remove air bubbles from uncured cement paste. The specimens were removed from the molds after 30 min and conditioned in distilled water at 37° C. for 1 day (23.5 h) and 7 days. Six specimens were made for each test. FIGS. 2A-2G shows the mechanical testing data.

Mechanical tests were performed on a screw-driven mechanical testing machine (Instron) with a crosshead speed of 0.5 mm min−1. The compressive strength was calculated. For the flexural strength test, each specimen was placed on an 8 mm diameter annular knife-edged support ring (Instron), and the load to fracture at the rate of 0.5 mm min−1, using a 3 mm diameter ball ended indenter in a universal load testing machine, was recorded. Each specimen was tested at least six times.

Example 6

Shear Bond Strength Measurement

In order to measure the bond strength, human extracted or impacted permanent third molars were stored and surface treated according to the previous procedures. The treated teeth were then mounted in resin holders and both buccal and lingual surfaces of each tooth were trimmed with a low-speed trimmer. Subsequently, median grit silicon carbide papers (Grade P600, 1500) were used to obtain smooth dentin surfaces. Both the PDA-GIC group and the control group (Fuji IX®) cement samples were mixed according to the manufacturer's instructions (instructions for the uncoated particles were applied for the coated particles as well). The samples were placed in a material holder (3.0 mm diameter×3.0 mm height). The samples were fitted by placing them in contact with the prepared dentin surfaces. The specimen assembly was then stored in 100% relative humidity at 37° C. for 1 h and then in distilled water for periods of 1 day, 7 days and 30 days.

After time intervals of 1 and 7 days of storage in distilled water, a shear load was applied to the glass ionomer/dentin interface using a standard mechanical testing machine with a knife-edged rod. All the mechanical testing machines were calibrated prior to starting the measurements. The shear force required to separate the cylinder from the dentine was recorded in Newtons and divided by the contact surface area, to determine the shear bond strength value in MPa. The debonded surfaces of the specimens were air dried and the mode of failure was determined using an SEM. The failure mode was classified according to one of following types: adhesive, cohesive in the cement, cohesive in dentin or mixed mode of failure.

Example 7

Microhardness Measurements

The Vickers hardness of the PDA-containing glass-ionomer samples was determined according to previously-reported methods, using a microhardness tester (Model MVK-E, M 400, Leco, St. Joseph, Mich., USA). A diamond indenter with 100 g load and a dwell time of 10 s were employed. Each of the five samples was indented two times, and the Vickers hardness number for each sample was calculated. The Vickers hardness values of the Fuji IX GP® samples were evaluated and used as the control.

Example 8

Characterization of Working Time and Initial Setting Time

The working and setting times were determined according to a method previously utilized (see below). After mixing the glass ionomer powder and liquid (in a 3.6/1 powder to liquid ratio), a small amount of the cement was mixed for 20 s, then placed between the plates of a rheometer and allowed to set. The working and setting times were determined by calculating the time taken to reach 95% and 5% of the initial amplitude of the oscillation. The values reported in are the average of five determinations. (see FIG. 2E).

This experiment was performed as follows: the rheometer has a spring that oscillates. When the unset cement was placed on the plate, the spring can move to 100% limit. When the cement starts setting (hardening) the spring starts to move less. When the amount of moving of the spring became 95% of original, it is the working time and when it was reduced to only 5% of original swing the cement is set.

Example 9

Nano-Indentation Analysis-AFM

Figure 9:
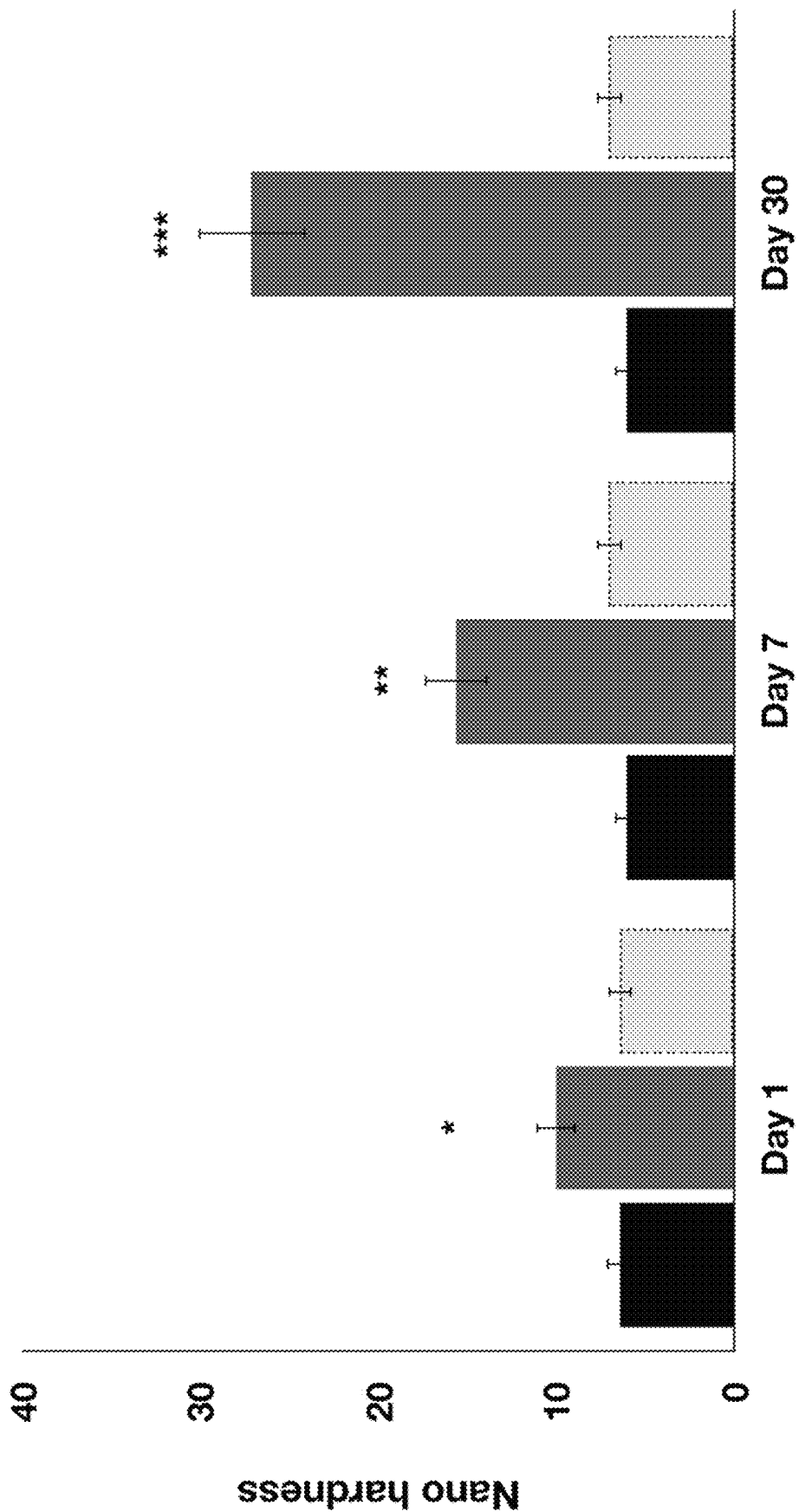
FIG. 9 Nano hardness properties of the carious dentin before and after bonding to PDA-GIC compared to Fuji IX® GIC after 1, 7, and 30 days. *p<0.05, p<0.01, and *p<0.001.

The efficiency of PDA containing GIC samples on the remineralization of the carious dentin was analyzed. Nanohardness of carious dentin before after application of PDA containing GIC were evaluated. Briefly, The PDA coated glass ionomer particles were mixed with polyacrylic acid and were applied on the surface of teeth with and without carious lesions. The tooth slices/PDA containing GIC were then immersed in 30 ml of artificial saliva (AS) solution (0.2 mM MgCl2, 1 mM CaCl2 H2O, 20 mM HEPES buffer, 4 mM KH2PO4, 16 mM KCl, 4.5 mM NH4Cl, 300 p.p.m. NaF, pH 7.0, adjusted with 1 M NaOH) at 37° C. for 1 and 7 days. After the allotted time the tooth slice was removed from the solution, rinsed with running deionized water for 50 s, air dried, and surface of the samples were polished using SiC abrasive papers from 800 up to 4000 grit. An atomic force microscope (AFM Nanoscope V, Digital Instruments, Veeco Metrology group, Santa Barbara, Calif.) was used to analyze the surface nano-hardness. Multiple indentations were done at different locations for carious dentin before and after PDA-GIC applications (at 3-time intervals: 1, 7, and 30 days). The data confirmed a significant increase in the surface nano hardness (nano-indentation) of carious dentin structure after only one week of presence of PDA-GIC (FIG. 9).

Example 10

Microtensile Bond Strength (uTBS) Test

Figure 10:
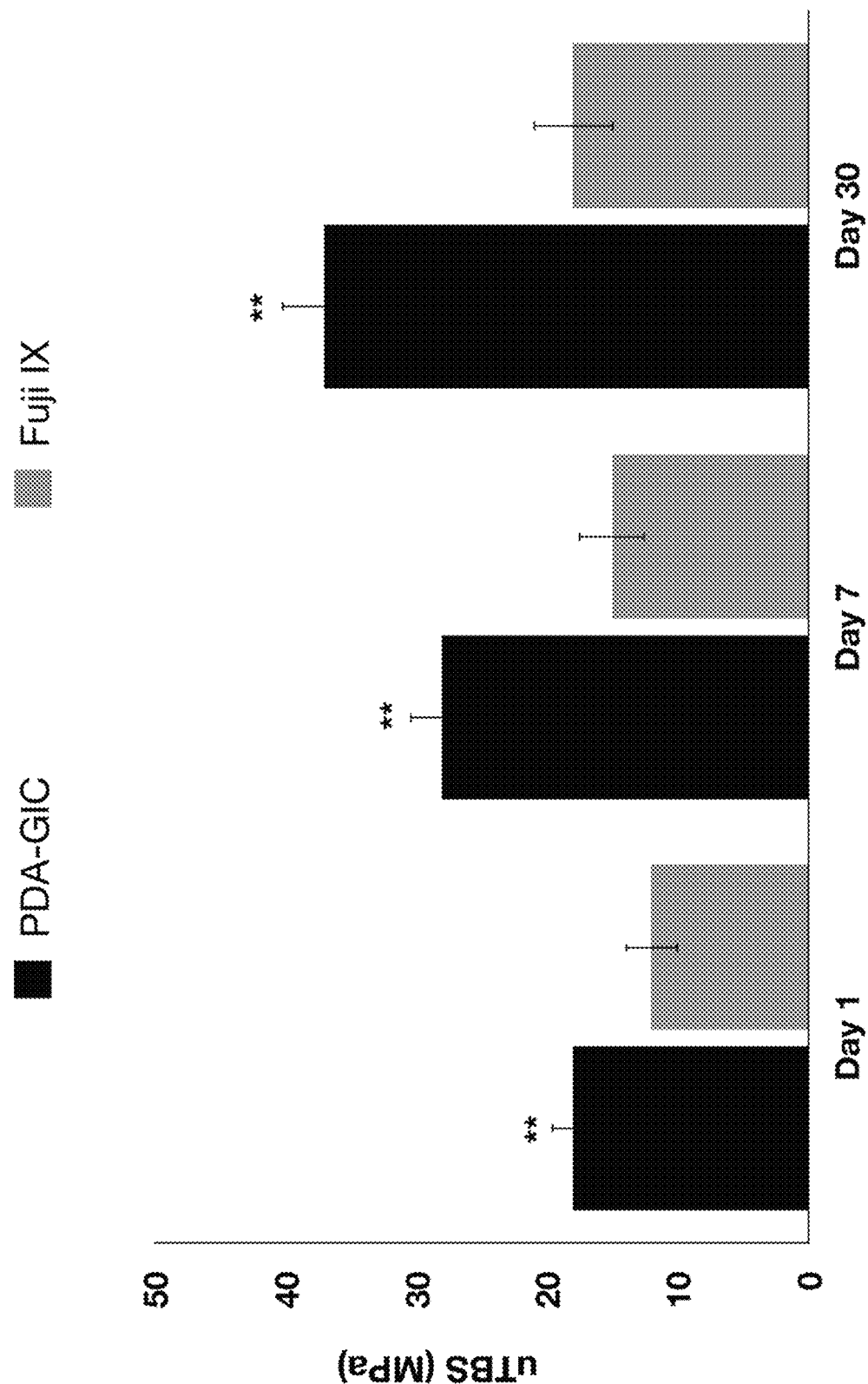
FIG. 10 Microtensile bond strength values (MPa) to dentin when bonded to PDA-GIC or to Fuji IX® GIC after 1, 7, and 30 days. **p<0.01.

In order to measure the microtensile bond strength, human permanent third molars buccal and lingual surfaces of each tooth were trimmed with a low-speed trimmer Subsequently, median grit silicon carbide papers (Grade P600, 1500) were used to obtain smooth dentin surfaces. Both the PDA-GIC group and the control group (Fuji IX) cement samples were mixed according to the manufacturer's instructions and put into a material holder (3.0 mm diameter×3.0 mm height). The specimen assembly was then stored in 100% relative humidity at 37° C. for 1 h and then in distilled water for periods of 23 h, 7 days and 30 days. Samples were tested using a microtensile bond strength-testing machine (Instron 4411, Instron Corporation, Canton, Mass., USA) at a crosshead speed of 0.5 mm/min. Bond strength data were calculated in MPa. The data clearly showed a significant increase in the uTBS of PDA containing GIC in comparison to the control group (FIG. 10).

Example 11

Biocompatibility and Dentinogenesis Properties of PDA Containing Glass Ionomer Cements PDA-GIC disk-shaped samples with 8 mm diameter with different ratios of PDA were fabricated, as discussed earlier. The specimens were sterilized with UV-Light for 1 hour. The sterilized disks were then used to study cellular behavior. Passage 5 Human dental pulp stem cells (DPSC) were cultured on the sterilized either PDA-GIC or control GIC (Fuji IX®) disks in regular cell culture media (a MEM, 15% FBS, 100 U/ml pen/strep, 2 mM Glutamax, 0.1 mM L-ascorbic acid) for two weeks.

Viability of cells was measured after 1 week and two weeks of incubation using LIVE/DEAD™ Viability/Cytotoxicity Kit, for mammalian cells (Invitrogen). After two weeks, the odontogenic differentiation of the DPSCs cultured on PDA-GI with different ratios were studied using qPCR. Fold change in expression of dentin sialophosphoprotein (DSPP), dentin matrix protein 1 (DMP-1) and matrix extracellular phosphoglycoprotein (MEPE) were measured as markers of odontogenic differentiation. All of the experiments have been repeated for 3 times. The data confirmed the biocompatibility of the inventive cement (FIGS. 7A-7I). Additionally, in the presence of PDA containing GIC, PDSC were differentiated toward odontogenic (dentin-like tissues) as was confirmed by significantly high levels of expressions for dentin DSPP, DMP-1, and MEPE (FIGS. 8A-8C).

'Different ratios of PDA' as noted herein above refers to the amount of coated GIC particles from the total of coated and uncoated particles, see for example description of FIGS. 8A-8C herein above.

Example 12

Application of Resin Comprising PDA

Application of PDA containing dental resin on white spots (dental caries in their initial steps) was performed. Comparison of the enamel surface with white spot (demineralized surface) after application of resin alone (negative control) and the resin containing PDA was presented. SEM analysis after 1 week in artificial saliva solution. The SEM analysis showed presence of hydroxyapatite deposition on the surface of PDA-containing resin (see FIG. 5B). Results were confirmed with XRD and EDX. This experiment confirmed the bioactivity and re-mineralization capability and potential of the novel cement. SEM images EHT=10.00 kV.

In this example, to form the resin containing PDA, the particles comprising PDA-coated GIC particles, were added to the resin prior to application. The resin functioned as a vehicle for the particles.

The presented data confirms the development of a new class of dental restorative materials with the in-situ remineralization ability. The material can be used as a direct dental or bone restorative material or can be used as liner or (in)direct pulp capping material. In comparison to the current glass ionomer materials available in the market, the disclosed material exhibits robust re-mineralization properties, exhibits improved mechanical properties (flexural strength and bond strength, and further offers fast setting times). In one illustration of the functional activities of this material, when the PDA-surface coated glass particles were incorporated into a resin and applied on the surface of enamel, a significant amount of mineralization has been observed (FIG. 5B). Therefore, this system can be used, for example, as novel treatment modality for teeth sensitivity or mineralization of teeth white spots.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A glass ionomer cement composition comprising fluoroaluminosilicate glass particles coated by polydopamine (PDA).

2. The composition of claim 1, wherein the thickness of the polydopamine coating layer ranges between 5 and 100 nanometers in thickness.

3. The composition of claim 1, further comprising fluoroaluminosilicate glass particles not coated by polydopamine.

4. The composition of claim 3, wherein, the relative amount of fluoroaluminosilicate glass particles coated by polydopamine is from 1% to 95% of the total fluoroaluminosilicate glass particles present in the composition.

5. The composition of claim 1, further comprising polyacid.

6. The composition of claim 5, wherein said polyacid is selected from polyacrylic acid, itaconic acid, maleic acid, tartaric acid or any combination thereof.

7. The composition of claim 1, further comprising a resin.

8. The composition of claim 7, wherein said resin is selected from HEMA (hydroxyethyl methacrylate), Bis-GMA (bisphenol A-glycidyl methacrylate), TEGMA (triethylene glycol dimethacrylate) or UDMA (urethane di-methacrylate resin) or any combination thereof.

9. The composition of claim 8, wherein the polydopamine-coated fluoroaluminosilicate glass particles are disposed within said hydroxyethyl methacrylate resin.

10. The composition of claim 9, wherein said hydroxyethyl methacrylate resin is light cured.

11. The composition of claim 4, wherein the composition exhibits a setting time of less than 5 minutes at 25° C.

12. The composition of claim 1, wherein said glass further comprises calcium, sodium, phosphate or a combination thereof.

13. The composition of claim 1, wherein said polydopamine comprises polydopamine HCl.

14. A method of using the cement composition of claim 3 in dentistry, the method comprising:
a) mixing said fluoroaluminosilicate glass particles coated by polydopamine (PDA) with said fluoroaluminosilicate glass particles not coated by polydopamine (PDA) to form a powder mixture;
b) disposing the formed mixture at an in vivo site.

15. The method of claim 14, further comprising:
removing caries from a tooth;
rinsing the cavity after caries removal;
mixing the powder comprising PDA-coated glass particles with a liquid comprising polyacid, wherein said mixing is conducted prior to, in parallel to, or following said step of rinsing the cavity after caries removal;
placing the PDA containing cement directly in the cavity;
such that said cement composition acts as a restorative material or as a cavity liner for said tooth.

16. The method of claim 14, further comprising:
mix the powder comprising PDA-coated glass particles with a liquid comprising polyacid to form a cement;
load a crown or restoration with said cement;
place said crown or restoration in a patient's mouth;
such that said cement composition acts as a luting element.

17. The method of claim 14, further comprising:
mix the powder comprising PDA-coated glass particles with a liquid comprising polyacid to form a cement;
remove caries in an incomplete manner such that a layer of affected dentin is kept;
apply said cement to said dentin layer;
such that said cement composition acts as a pulp capping.

18. The method of claim 14, further comprising applying said cement to a tooth such that said cement composition acts as a material to bond to carious lesions, a material to reduce teeth sensitivity, as a material to promote mineralization of teeth white spots or to any combination thereof.

19. A method of using the composition of claim 1 to generate a layer of hydroxyapatite at the surface of a tooth, said method comprising:
disposing the polydopamine-coated fluoroaluminosilicate glass particles of claim 1 in a resin to form a resin/particle composition;
applying the resin/particle composition to white spots on said surface of said tooth.

20. The method of claim 19, further comprising curing the resin/particle composition by light irradiation.

21. The composition of claim 4, wherein, the relative amount of fluoroaluminosilicate glass particles coated by polydopamine is from 1% to 50% of the total fluoroaluminosilicate glass particles present in the composition.

22. The composition of claim 21, wherein, the relative amount of fluoroaluminosilicate glass particles coated by polydopamine is from 8% to 30% of the total fluoroaluminosilicate glass particles present in the composition.

* * * * *